United States Patent [19]
Hahn et al.

[11] Patent Number: 6,139,850
[45] Date of Patent: *Oct. 31, 2000

[54] FORMULATIONS AND METHODS FOR REDUCING SKIN IRRITATION

[75] Inventors: Gary S. Hahn, Cardiff by the Sea; David O. Thueson, Poway, both of Calif.

[73] Assignee: Cosmederm Technologies, La Jolla, Calif.

[*] Notice: This patent is subject to a terminal disclaimer.

[21] Appl. No.: 08/860,993

[22] PCT Filed: Dec. 21, 1995

[86] PCT No.: PCT/US95/16985

§ 371 Date: Jun. 23, 1997

§ 102(e) Date: Jun. 23, 1997

[87] PCT Pub. No.: WO96/19184

PCT Pub. Date: Jun. 27, 1996

Related U.S. Application Data

[63] Continuation-in-part of application No. 08/362,100, Dec. 22, 1994, Pat. No. 5,716,625.

[51] Int. Cl.[7] .................................................. A61K 7/48

[52] U.S. Cl. .................... 424/401; 424/195.1; 514/847; 514/848; 514/859; 514/881; 514/887

[58] Field of Search .................................... 424/401, 617, 424/195.1; 514/847, 848, 859, 887, 881

[56] References Cited

U.S. PATENT DOCUMENTS

| | | | |
|---|---|---|---|
| 3,716,054 | 2/1973 | Porter et al. | 128/172.1 |
| 4,105,782 | 8/1978 | Yu et al. | 424/283 |
| 4,105,783 | 8/1978 | Yu et al. | 424/283 |
| 4,191,750 | 3/1980 | Hodosh | 424/127 |
| 4,285,973 | 8/1981 | Edwards | 424/358 |
| 4,388,301 | 6/1983 | Klein | 424/154 |
| 4,477,439 | 10/1984 | D'Alelio | 424/162 |
| 4,943,432 | 7/1990 | Biener | 424/647 |
| 4,971,800 | 11/1990 | Chess et al. | 424/449 |
| 5,262,153 | 11/1993 | Mishima et al. | 424/62 |
| 5,716,625 | 2/1998 | Hahn et al. | 424/407 |
| 5,804,203 | 9/1998 | Hahn et al. | 424/407 |
| 5,824,650 | 10/1998 | De Lacharriere et al. | 514/15 |
| 5,851,556 | 12/1998 | Breton et al. | 424/639 |
| 5,866,168 | 2/1999 | De Lacharriere et al. | 424/639 |
| 5,972,892 | 10/1999 | De Lacharriere et al. | 514/15 |

FOREIGN PATENT DOCUMENTS

| | | |
|---|---|---|
| 0 654 270 | 5/1995 | European Pat. Off. . |
| 2 590 273 | 5/1987 | France . |

OTHER PUBLICATIONS

Y. Zyuzyukin et al., "Local Action of Strontium Compounds," *Chemical Abstracts* 1973:12, pp. 100–101, Abstract No. 80:78918 (1973).

*The Merck Index*, 11th Ed., 1989, pp. 1394–1395.

Bilotto, Gerardo, et al., "Effects of Ionic and Non–Ionic Solutions on Intradental Nerve Activity in the Cat," *Pain*, 32: 231–238, 1988.

Celerier, et al., "Modulatory Effects of Selenium and Strontium Salts on Keratinocyte–Derived Inflammatory Cytokines," *Arch. Dermatol. Res.*, vol. 287, pp. 680–682 (1985).

Foreman, J.C. et al., "Movement of Strontium Ions into Mast Cells and its Relationship to the Secretory Response," *J. Physiol.*, 271:233–251, 1977.

Frankenhaeuser, Bernhard, et al., "The Effect of Magnesium and Calcium on the Frog Myelinated Nerve Fibre," *J. Physiol.*, 142: 360–365, 1958.

Gutentag, Herb, "The Effect of Strontium Chloride on Peripheral Nerve in Comparison to the Action of 'Stabilizer' and 'Labilizer' Compounds," *Penn. Dental Journal*, 68(2): 37–43, Feb. 1965.

(List continued on next page.)

Primary Examiner—Thurman K. Page
Assistant Examiner—L. Channavajjala
Attorney, Agent, or Firm—Lyon & Lyon LLP

[57] ABSTRACT

Composition and methods are provided for inhibiting skin irritation attributable to chemical irritants or environmental conditions, by the application of an anti-irritant amount of aqueous-soluble strontium cation.

113 Claims, 13 Drawing Sheets

OTHER PUBLICATIONS

Kato, G., et al., "Anaesthetic Action of Magnesium Ions," *Can. Anaes. Soc. J.*, 15(6): 539–544, Nov. 1968.

Kim, Syngcuk, "Hypersensitive Teeth: Desensitization of Pulpal Sensory Nerves," *J. Endodontics*, 12(10): 482–485, Oct. 1986.

Markowitz, K., et al., "Decreasing Intradental Nerve Activity in the Cat with Potassium and Divalent Cations," *Archs. Oral Biol.*, 36(1): 1–7, 1991.

Markowitz, K., et al., "The Role of Selected Cations in the Desensitization of Intradental Nerves," *Proc. Finn. Dent. Soc.*, 88 (Suppl I): 39–54, 1992.

Orchardson, R., "Is Calcium More Effective than Strontium as a Desensitizing Agent for Dentine?," in Lesney & Matthew (eds.), *Current Topics in Oral Biology*, Univ. of Bristol Press (Bristol, 1985), pp. 205–215.

Penny, Deborah, et al., "Fast Desensitization of Tooth Roots by Topically Applied $SnF_2$ and $SrCl_2$ in Dogs," *Archs. Oral Biol.*, 21(6): 339–347, 1976.

Shioya, Takao, et al., "Fast and Slow Blockades of the Inward–Rectifier $K^+$ Channel by External Divalent Cations in Guinea–Pig Cardiac Myocytes," *Pflugers Arch.*, 422: 427–435, 1993.

Sohn et al, "Agonist–Independent, Muscle–Type–Specific Signal Transduction Pathways in Cat Esophageal and Lower Esophageal Sphincter Circular Smooth Muscle," *J. Pharmacol. & Exp. Therap.*, vol. 273, No. 1, pp. 482–491 (1995).

Sohn et al, "Different Receptors Activate a Different Single G–Protein in Esophageal ($G_{i3}$) and in LES ($G_q$) Circular Smooth Muscle," *Gastroenterology*, vol. 104, abstract p. A585 (Apr. 1993).

Abel, Elizibeth, A., "Phototherapy", *Dematologic Clinics*, 13(4):841–849, Oct. 1995.

Arky, Ronald, et al. (Eds.), *Physicians Desk Reference*, $49^{th}$ Edition, 1995, p. 929.

Fitzpatrick, Thomas B., et al. (Eds.), *Dermatology in General Medicine*, (McGraw–Hill, Inc. 1993), $4^{th}$ Ed., vol. 1, pp. 501, 508–510, 1393–1396.

Gilman, Alfred Goodman, et al., *The Pharmacological Basis of Therapeutics*, (McGraw–Hill, Inc.,1993), pp. 769–771, 1291, 1518–1519, 1581,1586.

Gonzalez, Ernesto, "PUVA for Psoriasis," *Dermatological Clinics*, 13(4): 851–866, Oct. 1995.

Greaves, Malcolm W., et al., "Treatment of Psoriasis," *New England J. Med.*, 332(9):581–588, Mar. 1995.

Griffiths, Tamara W., et al., "Immunopathogenesis and Immunotherapy of Psoriasis," *Dermatological Clinics*, 13(4): 739–749, Oct. 1995.

Jeffes III, Edward W.B., et al., "Methotrexate and Other Chemotherapeutic agents Used to Treat Psoriasis," *Dermatologic Clinics*, 13(4): 875–890, Oct. 1995.

Katz, H. Irving, "Topical Corticosteroids," *Dermatologic Clinics*, 13(4): 805–815, Oct. 1995.

Koo, John, et al., "Cyclosporine: What Clinicians Need to Know," *Dermatologic Clinics*, 13(4): 897–907, Oct. 1995.

Kragballe, Knud, "Vitamin D3 Anaolgues," *Dermatologic Clinics*, 13(4): 835–839, Oct. 1995.

Lebwohl, Mark, "Future Psoriasis Therapy," *Dermatologic Clinics*, 13(4): 915–923, Oct. 1995.

Momtaz–T., Khosrow, "Modifications of PUVA," *Dermatologic Clinics*, 13(4): 867–873, Oct. 1995.

Silverman, A.K., et al., "Tars and Anthralins," *Dermatologic Clinics*, 13(4): 816–834, Oct. 1995.

Wieder, Joshua, M., et al., "Systemic Retinoids for Psoriasis," *Dermatologic Clinics*, 13(4): 891–896, Oct. 1995.

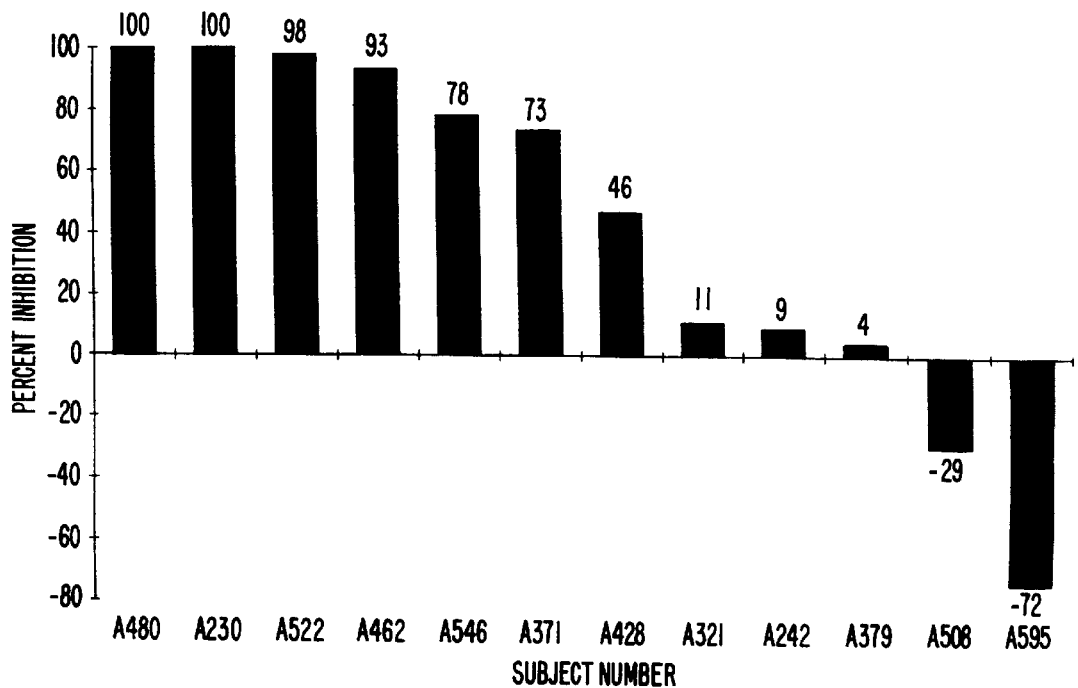
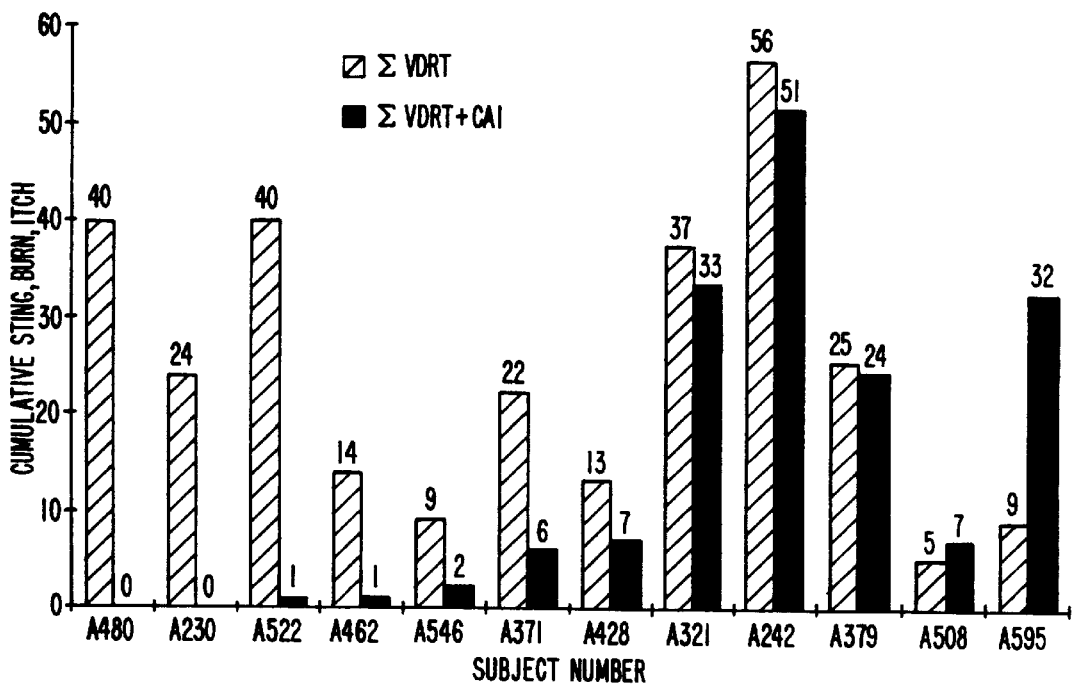

FORMULATIONS AND METHODS FOR REDUCING SKIN IRRITATION

This application is a continuation-in-part of Ser. No. 08/362,100, filed Dec. 22, 1994 and now U.S. Pat. No. 5,716,625. The present application was filed nationally on Jun. 23, 1997 pursuant to 35 U.S.C. § 371, based on International Application No. PCT/US95/16985 (filed Dec. 21, 1995). The aforesaid PCT application claims the benefit of the filing date of Ser. No. 08/362,100 (Dec. 21, 1994) pursuant to 35 U.S.C. §§ 120 and 365.

TECHNICAL FIELD

This invention relates to compositions and formulations, and methods for using the same, to inhibit skin irritation in animals.

BACKGROUND

Many substances are applied topically to the skin or mucous membranes of humans or animals (hereafter "skin") in order to alter the subject's appearance, to protect the subject from the environment, or to produce a biological change in the skin or other tissue for therapeutic, preventive or cosmetic purposes. These substances may generically be termed "topical products" and include such topically applied substances as cosmetics, over-the-counter and prescription topical drugs, and a variety of other products such as soaps and detergents.

Topical products occur in a variety of forms, including solids, liquids, suspensions, semisolids (such as creams, gels, pastes or "sticks"), powders or finely dispersed liquids such as sprays or mists. Examples of topical products commonly classified as "cosmetics" include skin care products such as creams, lotions, moisturizers and "treatment cosmetics" such as exfoliants and/or skin cell renewal agents; fragrances such as perfumes and colognes, and deodorants; shaving-related products such as creams, "bracers" and aftershaves; depilatories and other hair removal products; skin cleansers, toners and astringents; pre-moistened wipes and washcloths; tanning lotions; bath products such as oils; eye care products such as eye lotions and makeup removers; foot care products such as powders and sprays; skin colorant and make-up products such as foundations, blushes, rouges, eye shadows and liners, lip colors and mascaras; lip balms and sticks; hair care and treatment products such as shampoos, conditioners, colorants, dyes. bleaches, straighteners, and permanent wave products; baby products such as baby lotions, oils, shampoos, powders and wet wipes; feminine hygiene products such as deodorants and douches; skin or facial peels applied by dermatologists or cosmeticians; and others. Examples of topical products commonly classified as "topical drugs" are many and varied, and include over-the-counter and/or prescription products such as antiperspirants, insect repellents, sunscreens and sunburn treatments, anti-acne agents, antibiotics, topical respiratory agents, ocular drugs such as eyedrops and saline solutions, therapeutic retinoids, anti-dandruff agents, external analgesics such as capsaicin products, topical contraceptives, topical drug delivery systems, gastrointestinal agents such as suppositories, enemas and hemorrhoid treatments, reproductive system agents such as vaginal treatments, oral treatments such as lozenges, and many other products with therapeutic or other effects. Other topical products include hand, facial and body soaps and detergents and other forms of skin cleansers, as well as household detergents and many other household products such as solvents, propellants, polishes, lubricants, adhesives, waxes and others which are either applied topically or are topically exposed to the body during normal use.

In a large number of cases, topical products contain chemicals which may produce "irritation," including various inflammation symptoms or signs, when applied to the skin or mucosa ("skin"). The present invention is directed in part to compositions and methods for inhibiting the irritation associated with such topical products.

The occurrence, frequency and nature of topical-product-induced irritation often varies from user to user. The severity of irritation to the susceptible user may range from subclinical to mild to severe. Typical symptoms of "irritation" include itching (pruritus), stinging, burning, tingling, "tightness," erythema (redness) or edema (swelling). The irritation response may be due to the direct effect on the skin of certain topical product chemicals or to a response by the immune system directed toward the chemicals alone or in combination with skin components (e.g. antigens).

The sensation of itch is one of the most common skin problems experienced by humans and animals. Itch can be defined as a sensation which provokes the desire to scratch the site from which the sensation originates. All skin contains sensory nerves which can transmit itch or other sensory impulses in response to chemical irritation, environmental exposure or disease processes. Although the precise population of itch producing nerves have not been identified, the thinnest, unmyelinated nerve population, termed type C nociceptive neurons are thought to be the most important in producing the sensation. Itch: Mechanisms and Management of Pruritus. Jeffrey D. Bernhard. McGraw-Hill, Inc. (San Francisco, 1994), pp. 1–22. The sensory nerves of the skin can be considered to be a "final common pathway" for the many irritating conditions which may be ultimately sensed as itch including chemical exposure, environmental exposure (such as that which produces dry, itchy skin) and disease processes such as atopic dermatitis. Many chemical substances are able to produce itch or other sensory impulses when topically applied to the skin. No matter what the ultimate cause of itch, the sensation experienced is the same and provokes the desire to scratch.

Many ingredients used in topical products are known irritants or are potentially irritating, especially to people with "sensitive skin". These irritating ingredients include fragrances, preservatives, solvents, propellants and many other ingredients that might otherwise be considered inert components of the products. Additionally, many topical product active ingredients, including chemicals that may also be classified as drugs, produce irritation when applied to the skin. These include, but are not limited to, such ingredients as exfoliants and skin cell renewal agents, anti-acne drugs, antiperspirant compounds, antihistamines, anti-inflammatory agents, skin protective agents, insect repellent chemicals, sunscreens and many others. Where more than one chemical irritant is present, their irritating effects may be additive. Furthermore, chemical ingredients may react with one another, or in the environment of the skin, to form new chemicals which are irritating. The vehicles in which the active drug ingredients are formulated may also produce irritation in sensitive people, especially in the case of drugs such as topical corticosteroids.

In addition to chemicals which directly trigger skin irritation, some chemicals indirectly cause the skin to become more sensitive to other chemicals or environmental conditions which would not normally cause irritation. Many chemicals which act as skin "exfoliants" such as retinoids (e.g. tretinoin, retinol and retinal), carboxylic acids including α-hydroxy acids (e.g. lactic acid, glycolic acid), β-hydroxy acids (e.g. salicylic acid), α-keto acids, acetic acid and trichloroacetic acid, 1-pyrrolidone-5-carboxylic acid, capryloyl salicylic acid, αhydroxy decanoic acid, α-hydroxy octanoic acid, gluconolactone, methoxypropyl gluconamide, oxalic acid, malic acid, tartaric acid, mandelic acid, benzylic acid, gluconic acid, benzoyl peroxide and phenol, among others, may cause the skin to become more sensitive to irritation triggered by other topically-applied chemicals such as moisturizers, sunscreens, fragrances, preservatives, surfactants (e.g. soaps, shaving cream) and other topical products. Exfoliants and other ingredients may also increase the skin's sensitivity to environmental conditions such as sunlight, wind, cold temperature and dry air, or to chemical agents such as antigens, or may exacerbate the irritation attributable to a pre-existing skin disease.

Conversely, environmental influences may themselves increase the skin's sensitivity to chemicals in topical products by reducing the epidermal skin's "barrier function." The barrier function acts to minimize absorption or passage of potentially irritating chemicals through the outer "dead" cell layer of epidermal skin into the living skin tissue. Extremes of humidity, for example, can greatly increase irritation from topically-applied products. A very common condition due to low humidity is termed "winter itch" in which the very low humidity characteristics of many cold climates (particularly when accompanied by indoor heating) or long exposure to refrigerated air from air conditioners in the summer produces itchy skin—especially in older people—which can exacerbate the irritating effects of topical products. Additionally, soaps, detergents, cleansing products, shaving creams, alcohol and other products which remove some of the skin's protective lipids and/or secretions may increase the skin's permeability and sensitivity to topically-applied chemicals which would otherwise not produce irritation. Normal processes such as sweating may also increase the ability of irritant materials, such as antiperspirants, deodorants or sunscreens, to penetrate the skin through pores or glands, thus exacerbating the potential for irritation. Exposure of the skin to high humidity environments or liquids may also increase the ability of potential irritants to penetrate the skin. Similarly, the skin may become sensitized or inflamed due to infection, shaving abrasion, repeated or excessive washing or bathing, sun exposure, or other mechanical abrasion or injury, resulting in sensory irritation responses upon subsequent application of underarm deodorants, after-shaves or other topical products.

In addition to chemical and environmental causes of skin irritation, many people have an inherent sensitivity or genetic predisposition to skin irritants. People with respiratory allergies, for example, tend to have excessively dry skin which facilitates increased absorption of potentially irritating chemicals. The excessively dry skin which accompanies atopic dermatitis, for example, predisposes patients with this condition to irritation from many topically-applied products. Other skin diseases and conditions such as allergic or non-allergic contact dermatitis, asthma (including exercise-induced asthma as may be precipitated by inhalation of cold or dry air), rhinitis, conjunctivitis, inflammatory bowel disease, psoriasis, eczema, post-herpetic neuralgia, infectious diseases manifested by, for example, sore throat or skin lesions such as candidiasis, insect bites and the like produce intrinsic irritation which may be exacerbated by application of topical products or by exposure to chemical or environmental influences such as antigens, cold air, low humidity and the like. Many other individuals exhibit sensitive skin as a condition that is not related to an identifiable skin disease.

Whatever the exact cause of irritation, many attempts have been made to reduce the irritation potential of topical products by identifying chemicals which tend to cause irritation and reducing their concentration or eliminating them from the products. Many of these products are advertised to consumers as "hypoallergenic" or the like to designate a product's reduced tendency to cause irritation in consumers with sensitive skin. Many skin (including mucosal) irritation responses, however, are not allergic in origin. In any event, it is often not feasible or practical to identify or eliminate all of the irritating chemical(s), particularly when the irritating chemical(s) are the active ingredient of the product or are required for formulation, preservative or other functional reasons.

As one example, there is a substantial practical and commercial need in the field of exfoliants and related skin care products for a composition or method that will reduce or prevent the irritation caused by such products. Common exfoliants include α- and β-hydroxy carboxylic acids such as lactic acid, glycolic acid, salicylic acid and the like, α-keto acids such as pyruvic acid, as well as assorted compounds such as acetic acid and trichloroacetic acid, 1-pyrrolidone-5-carboxylic acid, capryloyl salicylic acid, α-hydroxy decanoic acid, α-hydroxy octanoic acid, gluconolactone, methoxypropyl gluconamide, oxalic acid, malic acid, tartaric acid, mandelic acid, benzylic acid, gluconic acid, peroxides, phenols, and skin cell renewal agents such as retinoids. Such products are used as exfoliants and/or cell renewal agents to reduce the occurrence or severity of skin wrinkles, particularly facial wrinkles, or as anti-acne, anti-"dry skin" or skin whitening agents. See U.S. Pat. Nos. 4,105,782, 4,105,783, 4,246,261, and 5,091,171 (Yu et al.) and U.S. Pat. No. 5,262,153 (Mishima et al.); W. P. Smith, "Hydroxy Acids and Skin Aging," Soap/Cosmetics/Chemical Specialties for September 1993, p. 54(1993). Hydroxy acids, in concentrations high enough to exfoliate, are well known often to cause skin irritation and rashes. The danger of irritation is even higher for persons that have sensitive skin.

Currently available methods reported by Yu et al. to reduce the irritation caused by hydroxy- and keto-acids in topical products include adding a strong alkali metal base such as sodium hydroxide or potassium hydroxide, thereby raising the pH of the preparation and reducing the acidity of the hydroxy acid. Such methods have the reported drawback of reducing the ability of the resulting hydroxy acid salt to penetrate the skin and thus compromising the beneficial effects (particularly anti-acne or anti-"dry skin" effects) of the hydroxy acid. Alternatively, Yu et al. have proposed the approach of formulating the hydroxy acid with a non-alkali metal base such as ammonium hydroxide or an organic base such as a primary, secondary or tertiary organic amine, thereby forming an amide or ammonium salt of the active ingredient hydroxy (or keto) acid. See U.S. Pat. Nos. 4,105, 782 and 4,105,783 (Yu et al.). The effect of such formulations is, again, to raise the pH of preparation to a non-irritating level. However, the increased pH (reduced acidity) of the resulting preparations renders them less efficacious as exfoliating or anti-wrinkle agents, which desirably have an acidity equivalent to pH 1–6. and more preferably pH 2–4. See Smith, above, at Table 1. Other approaches to reducing the irritation associated with exfoliant products include the use of slow-release topical formulations such as polymer-based vehicles (see, e.g., Chess et al., U.S. Pat. No. 4,971, 800) or microsponges, and inclusion of, e.g., plant-derived anti-irritant components (see, e.g., Smith et al., U.S. Pat. No. 5,028,428).

Mishima, et al. have reported that certain alkali or alkaline-earth metal salts of lactic acid were useful as skin-whitening agents (U.S. Pat. No. 5,262,153), but no recognition is expressed as to any need or ability to reduce irritation effects; in addition, the particular formulations of Mishima were typically "neutralized" or adjusted to pH 5.5 prior to screening or skin-whitening testing (see Experiments 1 and 2). A clear need exists, therefore, for a composition or method that prevents or reduces the skin irritation caused by low-pH (high-acidity) organic or inorganic acid products but that does not reduce the efficacy of the acids as exfoliant/cell-renewal agents.

More generally, it would be highly desirable to identify compounds with anti-irritant activities that would reduce the irritation caused by a wide range of otherwise safe and effective topical products, or to reduce the intrinsic irritation associated with various skin diseases and conditions (such as atopic or other dermatitis, asthma (including exercise-induced asthma), rhinitis or other respiratory inflammation, conjunctivitis, inflammatory bowel disease, eczema or psoriasis) or caused by exposure to irritating chemicals or environmental conditions such as antigens, sun, wind, cold air or extremes in humidity.

As explained in more detail below in the Detailed Description, the present invention involves the surprising discovery that the strontium metal cation of the invention is useful in reducing the incidence and severity of irritation associated with skin exposure to irritating chemicals or environmental conditions. While the exact mechanism (or mechanisms) of activity of this cation is not known and the invention is not limited to any particular mechanism, it is presently believed that the strontium cation may reduce irritation by interacting with skin nerve cells to prevent or counteract the sensation of irritation, and/or by interfering with irritation-inducing components of skin cells that are triggered by application of or exposure to the irritant. Thus, the cation may alter the ability of skin nerve cells to depolarize or repolarize, as for example by blocking or interfering with ion channel or pump operation or by altering the transmembranal action potential, or the cation may interfere with the transmission of nerve impulses from one nerve cell to another (as by suppressing neurotransmitter release). General descriptions of the function of channel proteins are given in B. Hille (ed.), *Ionic Channels of Excitable Membranes*, Sinauer Associates (Sunderland, Mass.: 2d Ed. 1992), and Siemen & Hescheler (eds.), *Nonselective Cation Channels: Pharmacology, Physiology and Biophysics*, Birkhauser Velgag (Basel, Switzerland: 1993). In addition, or alternatively, the strontium cation may act to inhibit or modify the action of skin cell proteases or other irritation-inducing biological molecules (such as eicosanoids or cytokines) that may otherwise be activated by topical application of skin irritants, or may alter "second-messenger" function within sensory cells.

A number of ionic species, and certain metal cations in particular, have been associated with various aspects of nerve cell activity. For example, during the resting (polarized) state of a typical nerve cell, the intracellular concentration of potassium in the nerve axon is high relative to the extracellular potassium concentration, and the intracellular concentration of sodium is low relative to the extracellular sodium concentration. During the process of nerve depolarization, potassium ions flow out of the cell across the membrane, and sodium ions flow into the cell, through pores created by axonal membrane proteins known as "channels". Following depolarization, membranal proteins known as ion "pumps" act to reestablish the resting, polarized state of the cell.

Other metal ions have also been shown to influence nerve function. For example, calcium ($Ca^{2+}$) is carefully regulated in higher eukaryotic organisms and is reported to have many important effects on cellular and neuronal activity. Calcium signaling pathways control many cellular processes, including fertilization, cell growth, transformation, secretion, smooth muscle contraction, sensory perception and neuronal signaling (Berridge, Nature 361(6410), 315–25 (1993)). The wide diversity of cells which display and use intercellular calcium waves and regulate calcium concentrations inside and outside the cell suggests that calcium levels provide a general mechanism by which cells communicate (Sanderson et al., Mol. Cell. Endocrinol. 98(2), 173–87 (1994)).

More particularly, calcium ion is a transducer of depolarization, and flows into the cell through a calcium channel during depolarization, although the amount of current flow varies from cell to cell (Stein, *Nerve and Muscle—Membranes, Cells and Systems*, pp.33–64 at p.56 (Plenum Press 1980); Forsen & Kordel, "Calcium in Biological Systems," in *Bioinorganic Chemistry* (Bertini et al., eds.), University Science Books (Mill Valley, Calif.: 1993), pp. 107–166). Several messenger pathways of intracellular calcium signal transduction also exist, such as inositol triphosphate-induced release of intracellular stores of calcium (Tsunoda, Biochim. Biophys. Acta. 1154(2), 105–56 (1993)). Calcium is a critical second messenger in virtually all cell types, and the signals generated by calcium can be single transients or prolonged elevations of intracellular calcium concentrations. Signaling patterns often vary from cell to cell and may contain more complex features such as calcium oscillations. Sub-cellular calcium signals and local concentration changes suggest even a further level of complexity and control of cell function and specialization. Nathanson, Gastroenterology 106(5), 1349–64 (1994).

Calcium also appears to modulate the release of neurotransmitters and, in a variety of cells, elevated calcium levels may result in stimulation of neurotransmitter release in some experimental systems. The divalent cations strontium and barium, while not normally found naturally in the body in physiologically significant amounts, may, by virtue of their atomic resemblance to calcium, similarly stimulate neurotransmitter release, whereas magnesium and manganese cations may have an inhibitory effect in the same system. Calcium is also involved in the postsynaptic action of neurotransmitters, and may also alter the activity of various nerve cell enzymes. Harris et al., J. Pharmacol. Exp. Therap. 195, 488–498 (1975).

Calcium, strontium, barium and certain other divalent cations have also been reported to modulate or block the gating and/or conductance properties of certain ion transporting proteins such as sodium and potassium channels (Shioya et al., Pflugers Arch. 422, 427–435 (1993); Cukierman, Biophys. J. 65, 1168–73 (1993); Marrero & Orkland, Proc. R. Soc. Lond. B. 253, 219–224 (1993)). One mechanism that has been proposed to explain these effects is that the cations may bind to the outer membrane of the nerve cell, thus altering the electric field locally near the membrane (Stein, above, at p.57); others have proposed models involving specific interactions between the divalent cations and the channel gate and/or pore (Shioya et al., above; Cukierman, above). Alternatively, the cations may regulate the function of many calcium-binding regulatory proteins such as calmodulin or may affect intracellular second messengers such as cyclic nucleotides ("Calcium: Controls and Triggers," in daSilva & Williams (eds.), *The Biological Chemistry of the Elements: The Inorganic Chemistry of Life*, Oxford University Press (New York: 1991), pp. 268–98).

Early studies involving selected nerve cell samples indicated that certain divalent cations, including magnesium and calcium, can have a "depressant" effect on nerve activity (Frankenhaueser & Meves, J. Physiol. 142, 360–365 (1958); Krnjevic, Brit. Med. Bull. 21, 10 (1965); Kato & Somjen, J. Neurobiol. 2, 181–195 (1969); Kelly et al., J. Neurobiol. 2, 197–208 (1969)). These results were generally attributed to post-synaptic membranal effects, as for example the inhibition of potassium or sodium currents in nerve samples exposed to the cations.

While laboratory studies such as these using cultured single cells or microelectrode single-cell electrophysiological techniques have done much to advance the understanding of nerve activity, distinct challenges are presented in the clinical setting. A number of factors make it difficult to predict what effects, if any, particular agents (cationic or otherwise) may have on nerve activity and sensation in intact animal bodies. For example, the animal body (and particularly the human body) contains a wide variety of nerve-containing tissues and organs adapted to perform many different and specialized functions. Other cells in the body—notably muscle cells and neuro-endocrine secretory systems—are "excitable" in a manner akin to nerve cell excitation. In order to achieve the disparate functions required in the animal body, the various tissues and organs are differently disposed within the body, and the nerves (and other excitable cells) within a given tissue are typically highly specialized as well as uniquely disposed within the particular tissue. As a result, different nerve-containing tissues may respond differently to a given agent depending on, for example, the type of nerve (or other excitable) cell and its structural disposition within the tissue, the mode of administration of the agent, the ability of the agent to penetrate to the respective nerve site, and the rate at which the agent is removed from the nerve site.

For example, while certain divalent cations including magnesium and calcium have long been reported in laboratory studies to have a "depressant" effect on nerves, clinical studies have shown that intravenously-administered magnesium sulfate produces neither anesthesia nor even analgesia in humans (Kato et al., Can. Anaes. Soc. J. 15, 539–544 (1968)). Instead, the magnesium ion induces paralysis of skeletal muscles, due perhaps to the inhibitory effects of magnesium on muscle cell activity. Oral ingestion of large doses of magnesium (e.g., magnesium sulfate as a laxative) does not result in paralysis or depressed neural activity in healthy individuals. On the other hand, when magnesium is applied directly to the brains of test animals, depressed neural or synaptic activity, and even a sleep-like state, reportedly result (Kato et al. (1968), above).

In addition, the mechanisms underlying sensory stimulation and perception in the animal body are diverse and exceedingly complex. Even within a single tissue or organ, different nerve groups having different organizations and functions may appear. Depending on how they are disposed within the tissue, the various nerve groups may be differently affected (or affected not at all) by an applied agent. Moreover, to the extent that different types of nerve cells occur within a tissue, they may have different susceptibilities to a particular applied agent. This is particularly true in the skin, which has nerves adapted to sense a wide variety of sensory inputs.

Another complicating factor arises from the detailed nature of nerve cell activity and response. The firing activity of an individual nerve cell may be influenced in a complex fashion, and may vary over time, depending on such factors as the extracellular and intracellular concentration of nerve-related ions as sodium, potassium, chloride, calcium and the like, as well as the time course of exposure to such ions. Other bioactive agents, such as prostaglandins present during inflammatory responses, may further influence nerve sensitivity. In addition, nerves may respond to non-chemical stimuli such as hydrodynamic pressure changes, which in turn may depend on the nature of the tissue in which the nerve is disposed. Such factors lead to considerable clinical uncertainty as to how various agents may affect nervous responses such as pain responses.

For example, studies have been undertaken over the last several decades in an effort to identify and elucidate the effects of various putative tooth-desensitizing agents and therapies. Tooth nerves are disposed primarily in the central pulp of the tooth, but also extend partially into the surrounding "dentin" material. The dentin material is a mineralized collagen matrix containing microscopic, fluid-filled "dentinal tubules." It has long been known that tooth nerve activity (which is sensed as pain) may be triggered by hydrodynamic pressure changes in the tubule fluid, as may be caused for example by probing or air-blasting the tooth or by applying an ionic solution having a high osmotic pressure (particularly when the protective enamel surrounding the dentin is degraded). Accordingly, one reportedly effective treatment for tooth hypersensitivity involves sealing or occluding the dentinal tubules using chemical or physical means (Scherman & Jacobsen, J. Am. Dent. Ass. 123, 57–61 (1992)). In addition, potassium and strontium salts, particularly potassium nitrate and strontium chloride, have been employed in dentifrices and are reported to reduce tooth sensitivity following two to six weeks of continuous use (Scherman & Jacobsen, above; Silverman, Comp. Cont. Dent. Educ. 6, 131–136 (1985)). One mechanism commonly advanced to explain this putative desensitizing activity is that precipitated potassium or strontium ions block or inhibit fluid flow within the dentinal tubules (Scherman & Jacobsen, above; Knight et al., J. Periodontal Res. 64, 366–373 (1993)). This explanation is consistent with the chemical/physical sealing therapies noted above, and also appears consistent with the clinical observation that several weeks of treatment are required in order to achieve substantial desensitizing effects.

A number of studies have attempted to elucidate other possible effects of various ions on tooth nerve activity, and have established that such effects may vary greatly depending on the clinical or experimental system employed. For example, pain is induced when potassium ion is applied to exposed tooth pulp but not when applied to the dentin (Nahri et al., Arch. Oral Biol. 27, 1053–58 (1982). Hypertonic solutions of calcium and magnesium salts have been reported to evoke pain and/or transient nerve electrical activity when applied to the dentin, probably due to dentinal tubule water movement induced by osmotic pressure effects (Orchardson, in Lisney & Matthew (eds.), Current Topics in Oral Biology, University of Bristol Press (Bristol: 1985), pp. 205–215; Nahri, above; Markowitz & Kim, Proc. Finn. Dent. Soc. 88 (Supp. 1), 39–54 (1992)). On the other hand, electrical activity studies undertaken on exposed tooth nerves (obtained, for example, by deeply abrading the dentin material) have indicated that various divalent cations (particularly calcium and magnesium) may suppress nerve electrical responses, while monovalent potassium evokes a transient electrical response followed by inhibition of excitability (Markowitz & Kim, above; Orchardson, above). In the final analysis, the Markowitz and Kim group concluded that it is difficult to explain the clinical desensitizing effects of the available ionic desensitizing dentrifices (which require several weeks of treatment) in terms of a direct nerve cell membrane function, and that studies undertaken with exposed nerves may not reflect the pain-induction mechanisms observed clinically (Markowitz & Kim, above).

The human skin presents a sensory and structural environment that is much more complicated than that of the tooth. For example, the skin contains nerves and highly specific sensory organs that are specialized and disposed so as to differentiate the stimuli leading to such distinct sensations as heat, cold, pressure, pain, itch and the like. In addition to normal sensory stimuli, nerves in the skin are also responsive to native or foreign chemicals such as proteases, prostaglandins, complement-system molecules, allergens, mitogens and the like which may be presented due to tissue injury or environmental exposure. Agents which are effective to combat one source of sensory stimulus—for example steroidal agents to treat skin inflammation—are ineffective against other sensory stimuli such as pressure, heat, or the transitory sting or itch caused by an applied skin care product. Conversely, local anesthetic agents which are effective to depress all sensory or even motor activity in a treated region are not desirable if only a single sensation—for example a transitory sting or itch—is sought to be eliminated. To complicate the situation, the structural matrix of the epidermal skin affords a "barrier function" which tends to exclude or inhibit the entry of foreign material, including potentially therapeutic agents.

Accordingly, it would be desirable to identify agents which are effective in the skin to inhibit certain identified sensory responses (as for example pain or itch) while not adversely affecting other nervous responses in the same tissue (as for example tactual sensations).

SUMMARY OF THE INVENTION

The present invention is directed to the use of the divalent cation strontium ($Sr^{2+}$) and salts thereof as ingredients to provide fast-acting, efficient and safe topical skin anti-irritant effects, and to formulations containing this cation. It is one object of the present invention to provide ingredients, formulations and methods of use which can suppress skin irritation due to chemical or environmental exposure, or due to tissue inflammation, injury or other skin pathology. The invention is particularly useful for preventing, reducing or eliminating the potential irritation caused by topical application of products containing other irritating ingredients, including especially cosmetics such as hydroxy acid or other exfoliant containing products, facial peels, shaving products, sunscreen products, deodorants and other cosmetics as described above, as well as topical drug products containing irritating active ingredients or vehicles, and other products such as soaps, detergents, solvents and the like which are either applied topically or are topically exposed to the body during use. Thus, the present invention meets a clear need for formulations and ingredients that will prevent or reduce the potential skin irritation caused by topical products. The invention is also useful for preventing, reducing or eliminating the skin irritation caused by skin diseases or other conditions such as environmental exposure to irritating chemicals or influences such as wind, heat, cold and extremes in humidity, including the intrinsic irritation associated with these conditions as well as such irritation as may be exacerbated by the application of a topical product.

Preferred embodiments of the present invention utilize an anti-irritant amount of the strontium cation accompanied (as in the form of a salt) by one or more ionizing anionic species, preferably an acidic anion species such as a chloride, nitrate, sulfate, acetate, gluconate or oxalate anion, dissolved or dispersed in an appropriate vehicle. Investigations relating to the present invention have shown that the anti-irritant effects of the cations of the invention can be optimized by suitable selection of the accompanying anionic species. Especially preferred cation-anion pairs include strontium chloride, strontium nitrate, and strontium acetate.

In the preferred embodiments, the cation of the invention is included in a suitable topical vehicle at a concentration of about 10 to about 3000 mM, more preferably about 50 to about 2000 mM, and most preferably about 100 to about 1000 mM. The most highly preferred concentration range in many instances is from about 250 to about 500 mM, as for example where the formulation of the invention includes an irritant ingredient such as an exfoliant ingredient. The appropriate cation concentration can be achieved, for example, using a single strontium salt, or multiple different cation salts may be combined to yield the total desired cation concentration.

In another preferred embodiment, the strontium cation of the invention is combined in a topical product formulation further comprising a potentially irritating ingredient, the cation being present in a total amount effective to reduce or eliminate irritation due to the irritant ingredient.

In another preferred embodiment, the cation of the invention is paired with one or more anionic species selected so as to achieve a desired level of acidity or basicity in the formulated composition, and a total cation concentration effective to reduce skin irritation. In one such particularly preferred embodiment, strontium is combined in a hydroxy acid or other exfoliant preparation accompanied by one or more suitable anionic species such that the pH of the hydroxy acid preparation is maintained in the range of pH 1–6, and more preferably in the range of pH 2–4. It will be understood that, where the formulation employs an anhydrous vehicle, the acidity of the formulation may not be expressible in typical pH terms, but that such acidity will manifest itself upon exposure of the formulation to the skin where water is present both intracellularly and extracellularly.

In another embodiment, the cation of the present invention may be combined in a formulation with other anti-irritants, such as steroidal or non-steroidal anti-inflammatory agents or other materials such as aloe vera, chamomile, α-bisabolol, Cola nitida extract, green tea extract, tea tree oil, licorice extract, allantoin, urea, caffeine or other xanthines, glycyrrhizic acid and its derivatives, or with other anti-irritant species such as those identified in co-pending U.S. patent application Ser. Nos. 08/362,101 now abandoned, 08/362,097 now abandoned, 08/362,058, now abandoned and 08/362,055 (entitled "Formulations and Methods for Reducing Skin Irritation"), filed on Dec. 21, 1994, now patent 5,756,107 by the present inventors, so as to achieve a multiple anti-irritant effect.

The invention further provides methods of treating, reducing or eliminating skin irritation comprising the topical application of a formulation comprising an anti-irritant effective amount of strontium. The cation formulation may further include one or more potentially irritating components. Alternatively, the cation formulation may be applied separately and prior to application of another product containing a potentially irritating component, or the cation formulation may be applied alone in order to prevent the development of irritation or to treat a pre-existing irritation attributable to conditions such as skin disease, chemical irritant exposure or environmental exposure.

DESCRIPTION OF THE DRAWINGS

FIGS. 5 through 8 depict experimental data showing the time course of irritation responses (FIG. 5), the cumulative irritation over time (FIG. 6), and the subject-by-subject cumulative irritation suppression and irritation responses (FIGS. 7 and 8) for a panel of humans treated with 250 mM strontium nitrate (and control) in a capsaicin skin irritation challenge.

DETAILED DESCRIPTION

Figure 1:
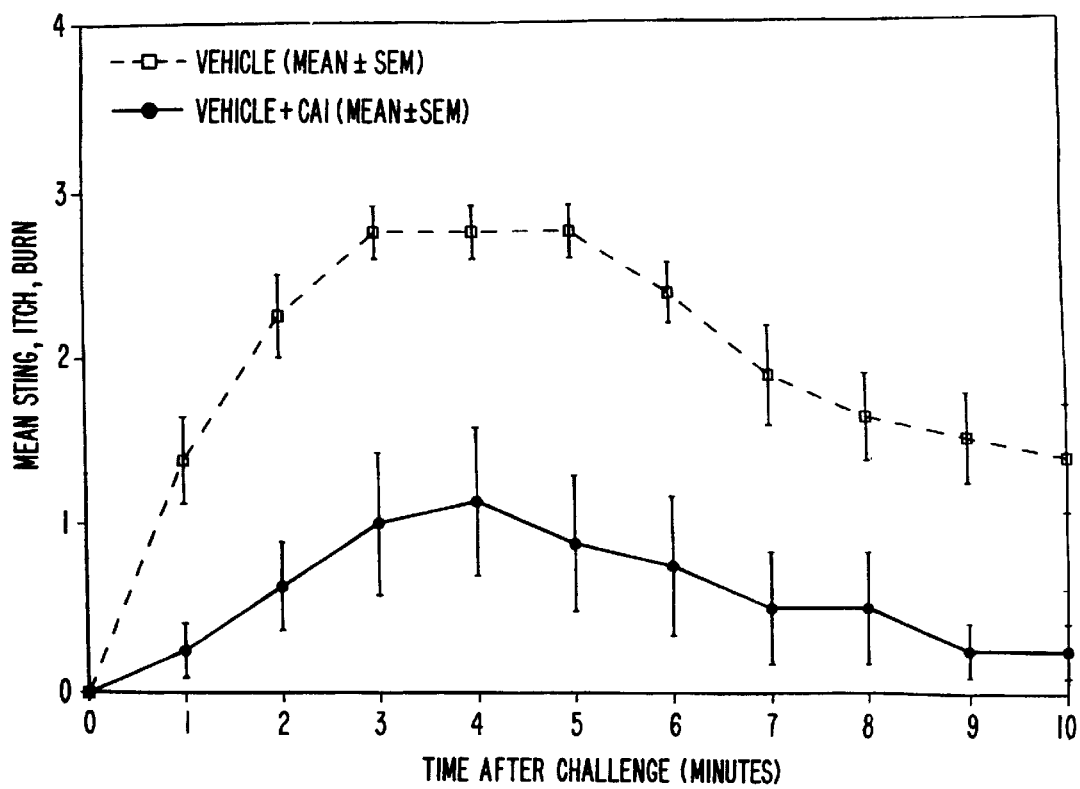
FIGS. 1 through 4 depict experimental data showing the time course of irritation responses (FIG. 1), the cumulative irritation over time (FIG. 2), and the subject-by-subject cumulative irritation suppression and irritation responses (FIGS. 3 and 4) for a panel of humans treated with 250 mM strontium nitrate (and control) in a lactic acid skin irritation challenge.

Human clinical trials undertaken in connection with the present invention have established that the cation species strontium(II) ($Sr^{2+}$) is effective, when applied topically to the skin in appropriate concentrations and vehicles, to suppress the relatively severe stinging, burning, tingling, itching and/or erythema induced by topical application of the hydroxy acid skin irritant lactic acid as well as the skin irritants glycolic acid, capsaicin, capryloyl salicylic acid, benzoyl peroxide, and post-shaving-applied seawater. Formulations containing the strontium cation are useful in suppressing a wide range of topical-product-induced irritation responses attributable to exfoliants, sunscreens, retinoids, anti-perspirants, deodorants, anti-acne and other products which contain components potentially capable of causing sensory irritation. For example, the cation of the present invention is useful for preventing or reducing the skin irritation caused by α- or β-hydroxy acids, α-keto acids and other carboxylic acids, as well as retinoids, phenols, peroxides and similar irritants found in over-the-counter topical products for home or cosmetologist use (such as, 1-pyrrolidone-5-carboxylic acid, capryloyl salicylic acid, α-hydroxy decanoic acid, α-hydroxy octanoic acid, gluconolactone, methoxypropyl gluconamide, oxalic acid, malic acid, tartaric acid, mandelic acid, benzylic acid, and gluconic acid), as well as in certain prescription topical drugs containing high (for example, 12% w/w or even higher) dosage forms of such irritants. The irritation attributable to combinations of such irritating ingredients, such as lactic acid/salicylic acid combinations and hydroxy acid/retinoid combinations, as well as irritation attributable to purified isomeric forms of such ingredients, can also be inhibited by the formulations of the invention. Additionally, formulations containing the cation are useful in ameliorating irritation in conditions where the skin is inherently hypersensitive to topical products (e.g. dry skin, "winter itch," and other inflammation or injury conditions) and in ameliorating the irritation due to such conditions even in the absence of other applied topical products. The formulations are also useful in treating non-human animal skin irritation, as for example dog or cat irritation and resultant scratching due to fleas or other skin disease or condition.

An additional benefit of the present anti-irritant compounds and formulations is that they do not have the undesirable anesthetic side-effects exhibited by Lidocaine and other similar skin local anesthetics. Upon application of a solution of the compound used in the clinical trials described here, subjects typically reported no sensations other than those sensations caused by the vehicle alone, and no lack of normal sensations.

Formulations of the Invention

The anti-irritant topical formulations of the invention comprise a topical vehicle suitable for administration to the animal (particularly human) skin, and an amount of the strontium cation effective to reduce, inhibit or eliminate existing or potential skin irritation. The cation component is, of course, accompanied in the formulation by one or more charge-neutralizing anionic counterions, although the cation-anion pairs as originally incorporated into the vehicle may become dissociated in the resulting formulation, or the strontium cations may become associated in the formulation with other anionic species appearing in the overall formulation. In one embodiment, the anti-irritant topical formulations additionally contain an irritant ingredient(s) that is itself capable of inducing skin irritation such as symptoms associated with inflammation, as for example a cosmetic or skin care product ingredient, or a pharmaceutically active ingredient or drug ingredient.

The topical anti-irritant formulation of the invention contains the divalent cation strontium ($Sr^{2+}$) in a concentration effective to prevent or reduce (hereafter, "inhibit") the skin irritation (such as inflammation) symptoms that are sought to be eliminated. The formulation preferably contains this cation component in a suitable topical vehicle at a total concentration of about 10 to about 3000 mM, more preferably about 50 to about 2000 mM, and most preferably about 100 to about 1000 mM. The most highly preferred concentration range in many instances is from about 250 to about 500 mM, as for example where the formulation of the invention includes an irritant ingredient such as an exfoliant ingredient. These preferred concentration ranges correspond to bioavailable forms of such cations within the formulation, particularly, ionizable and aqueous-soluble forms of the strontium cation as contrasted with insoluble or covalently-bonded forms of the cation. If other anti-irritant compounds are included in the formulation, then lower concentrations of the cations of the invention may be utilized.

Preferred cation concentrations can also be expressed in weight/volume or weight/weight percentage terms which will vary somewhat depending on the density of the vehicle and other components in the formulation. Thus, to take an example in which the vehicle has a density of 0.93 g/ml (as in a 50:50 [by volume] mixture of 95% ethyl alcohol and water) and the cation component is incorporated in the form of strontium nitrate (formula weight 212), representative molarity concentration values correspond approximately to

| 10 mM:   | 0.21% (w/v)  | 0.23% (w/w)  |
|----------|--------------|--------------|
| 50 mM:   | 1.05% (w/v)  | 1.14% (w/w)  |
| 100 mM:  | 2.1% (w/v)   | 2.28% (w/w)  |
| 250 mM:  | 5.3% (w/v)   | 5.7% (w/w)   |
| 500 mM:  | 10.5% (w/v)  | 11.4% (w/w)  |
| 1000 mM: | 21.2% (w/v)  | 22.8% (w/w)  |
| 1500 mM: | 31.7% (w/v)  | 34.2% (w/w)  |

The preferred concentration ranges expressed above contemplate that a typical topical dosage will be approximately 0.5 grams of cation formulation over a 5 cm×5 cm area of skin (25 cm$^2$). Clinical studies have shown that such preferred concentration ranges are generally effective to inhibit skin irritation and, in typical topical vehicles, are readily formulated and do not leave any significant visible residue when applied to the skin. Higher concentration formulations, such as saturated pastes or other forms, may also be successfully used, particularly where visible appearance is not a limiting consideration (as in therapeutic applications).

Furthermore, routine clinical assessments such as those described below can readily be employed to optimize the cation concentration and to ascertain if lower, or higher, concentrations are appropriate for a given formulation or irritation indication. For example, the concentration of cation may be adjusted to account for the amount of formulation that is typically applied to a given skin area by the user, which will depend to an extent on the physical nature of the topical vehicle (e.g., lotion as compared to liquid spray vehicles). Likewise, the amount of cation required may be reduced in such cases where the formulation contains a skin penetration-enhancing ingredient or other agent which increases the ability of the cations to permeate the stratum corneum to their site of anti-irritant activity. Preferably, the formulations of the invention include an amount of anti-irritant cation capable of inhibiting irritation in susceptible individuals by at least about 20% or more, as measured by a mean reduction in cumulative irritation across a susceptible test population as exemplified in the clinical protocols described below. Alternatively, the formulations of the invention include an amount of anti-irritant cation capable of inhibiting irritation by at least about 40% or more in at least about 10% of the susceptible population, as measured by a reduction in cumulative irritation on an individual-by-individual basis (treated vs. control areas). This latter measure of efficacy reflects the fact that the present formulations, similar to many therapeutic products, may in some cases be effective in delivering a significant benefit to some, but not all, of the susceptible population.

The optimum concentration of a cation of the invention may also be reduced below (or within) the preferred ranges set forth above if some other anti-irritant component is included in the formulation along with the cation component of the invention. In particular, it is contemplated that lower (e.g. halved) amounts of strontium ($Sr^{2+}$) cations may be used, while still maintaining comparable levels of anti-irritant activity, by further including an approximately equal concentration of, for example, a potassium channel mediating, regulating or blocking agent, a calcium channel blocking or regulatory agent, or a sodium channel blocking agent, or other anti-irritant agent such as a steroid or non-steroidal anti-inflammatory agent. Examples of suitable additional anti-irritant ingredients are described in applicants' co-pending U.S. patent application Ser. Nos. 08/362,101 now abandoned, 08/362,097 now abandoned, 08/362,058 now abandoned and 08/362,055 (entitled "Formulations and Methods for Reducing Skin Irritation"), filed Dec. 21, 1994 now U.S. Pat. No. 5,756,107 and incorporated by reference in their entirety. Other anti-irritant ingredients, such as aloe vera, chamomile, α-bisabolol, Cola nitida extract, green tea extract, tea tree oil, licorice extract, allantoin, urea, caffeine or other xanthines, and glycyrrhizic acid and its derivatives, may also be beneficially incorporated into the formulations of the invention in order further to inhibit irritation effects or symptoms.

The cation component of the invention is typically incorporated into the present formulations by mixing an appropriate amount of a suitable salt form of the cation into the chosen formulation vehicle, along with such other skin care components as are desired. From a formulation standpoint, it is preferred that the selected salt be sufficiently soluble in the formulation vehicle as to allow a consistent formulation having the desired physical and topical application characteristics. It will be recognized that, depending on the formulation vehicle chosen, the salt form of the cation of the invention may dissociate within the formulation (and in this case may associate with other anions also present in the formulation), or the salt form may remain substantially associated. It is also highly preferred that the salt (or salts) chosen be sufficiently aqueous-soluble such that, upon application to the skin, the component cations (and corresponding counteranions) can dissociate and be taken up into the water-containing milieu of the skin. In addition, it will be clear that the particular salt ingredient(s) chosen should be topically acceptable and preferably will not themselves be irritating toxic or otherwise deleterious to the user.

With these considerations in mind, it will be recognized that a variety of topically acceptable strontium/counteranion salt ingredients may be utilized in the present formulations in order to achieve the objectives of the invention. Such salts can be readily identified by those skilled in the art in view of the present disclosure based on known physical (e.g., solubility), pharmacological and toxicological information and, if necessary, by the application of routine experimentation.

Examples of potentially suitable counteranion components for use with the strontium cations of the invention include a variety of mono-, di- and trivalent inorganic and organic anions. Examples of potentially suitable inorganic anions include nitrate, sulfate, halogens (particularly F, Cl, Br and I), carbonate, bicarbonate, hydroxide, oxide, peroxide, nitrite, sulfide, bisulfate, persulfate, glycerophosphate, hypophosphate, borate and titanate. Examples of potentially suitable organic anions include carboxylic acids, alkoxylates, amino acids, peptides, saturated and unsaturated organic acids, and saturated and unsaturated fatty acids. Particular examples include citrate, oxalate, acetate, gluconate, lactate, tartrate, maleate, benzoate, propionate, salicylate, ascorbate, formate, succinate, folinate, aspartate, phthalate, oleate, palmitate, stearate, lauryl sulfate, lanolate, myristate, behenate, caseinate, cyclamate, pantothenate, EDTA and other polyaminopolycarboxylates, saccharin, thioglycolate, laurate, methylparaben, propylparaben, ricinoleate and sorbate anions. It will be recognized in view of the foregoing disclosure that certain of these suitable anion components, particularly various carboxylic acid anions, are themselves known active ingredients in various topical products (e.g. exfoliant products), and it will be seen accordingly that such active ingredients anions can be incorporated into useful formulations along with the anti-irritant counter-cations of the invention.

Clinical trials relating to the invention have established that certain cationanion pairs are particularly active as anti-irritants. These include strontium chloride, strontium nitrate, and strontium acetate.

Also preferred are these and other cation-anion pairs in which the anionic species is acidic, because such pairs will generally exhibit higher solubility in many common topical vehicles and suitable ionization upon application to the skin. In addition, strongly acidic anion components may be useful where it is desired to maintain the pH of the resulting formulation at a relatively acidic level, as for example in the case of hydroxy-acid or other acidic exfoliant products where the activity of the product to reduce wrinkles or bring about other beneficial effects may be reduced if the formulation is not relatively acidic. In any event, however, the desired level of acidity in such cases can be achieved by adjusting the formulation with a suitable acid (or base if necessary).

In one such particularly preferred embodiment, the strontium cation component of the present invention is combined in a hydroxy acid or other exfoliant preparation accompanied by one or more suitable anionic or other acidic species such that the pH of the hydroxy acid preparation is maintained in the range of pH 1–6, and more preferably in the range of pH 2–4. It will be understood that, where the formulation employs an anhydrous vehicle, the acidity of the formulation may not be expressible in typical pH terms, but that such acidity will manifest itself upon exposure of the formulation to the skin where water is present both intracellularly and extracellularly.

Suitable topical vehicles for use with the formulations of the invention are well known in the cosmetic and pharmaceutical arts, and include such vehicles (or vehicle components) as water; organic solvents such as alcohols (particularly lower alcohols readily capable of evaporating from the skin such as ethanol), glycols (such as glycerin), aliphatic alcohols (such as lanolin); mixtures of water and organic solvents (such as water and alcohol), and mixtures of organic solvents such as alcohol and glycerin (optionally also with water); lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile) such as cyclomethicone, demethiconol and dimethicone copolyol (Dow Corning); hydrocarbon-based materials such as petrolatum and squalene; anionic, cationic and amphoteric surfactants and soaps; sustained-release vehicles such as microsponges and polymer matrices; stabilizing and suspending agents; emulsifying agents; and other vehicles and vehicle components that are suitable for administration to the skin, as well as mixtures of topical vehicle components as identified above or otherwise known to the art. The vehicle may further include components adapted to improve the stability or effectiveness of the applied formulation, such as preservatives, antioxidants, skin penetration enhancers, sustained release materials, and the like. Examples of such vehicles and vehicle components are well known in the art and are described in such reference works as *Martindale— The Extra Pharmacopoeia* (Pharmaceutical Press, London 1993) and Martin (ed.), *Remington's Pharmaceutical Sciences*.

The choice of a suitable vehicle will depend on the particular physical form and mode of delivery that the formulation is to achieve. Examples of suitable forms include liquids (including dissolved forms of the cations of the invention as well as suspensions, emulsions and the like); solids and semisolids such as gels, foams, pastes, creams, ointments, "sticks" (as in lipsticks or underarm deodorant sticks), powders and the like; formulations containing liposomes or other delivery vesicles; rectal or vaginal suppositories, creams, foams, gels or ointments; and other forms. Typical modes of delivery include application using the fingers; application using a physical applicator such as a cloth, tissue, swab, stick or brush (as achieved for example by soaking the applicator with the formulation just prior to application, or by applying or adhering a prepared applicator already containing the formulation—such as a treated or premoistened bandage, wipe, washcloth or stick— to the skin); spraying (including mist, aerosol or foam spraying): dropper application (as for example with ear or eye drops); sprinkling (as with a suitable powder form of the formulation); soaking; and injection (particularly intradermal or subcutaneous injection). Iontophoresis or other electromagnetic-enhanced delivery systems may also be usefully employed, as for example to increase delivery to the dermis.

Methodologies and materials for preparing formulations in a variety of forms are also described in Anthony L.L. Hunting (ed.), "A Formulary of Cosmetic Preparations (Vol. 2)—Creams, Lotions and Milks," Micelle Press (England, N.J. 1993). See, for example, Chapter 7, pp. 5–14 (oils and gels); Chapter 8, pp.15–98 (bases and emulsions); Chapter 9, pp.101–120 ("all-purpose products"); Chapter 10, pp. 121–184 (cleansing masks, creams, lotions); Chapter 11, pp. 185–208 (foundation, vanishing and day creams); Chapter 12, pp. 209–254 (emollients); Chapter 13, pp. 297–324 (facial treatment products); Chapter 14, pp.325–380 (hand products); Chapter 15, pp.381–460 (body and skin creams and lotions); and Chapter 16, pp.461–484 (baby products); the contents of which are incorporated herein by reference.

The formulations of the invention are most preferably formulated such that the cation component of the formulation (as occurring with any accompanying anion counterion components) is substantially invisible upon application to the skin. This is particularly true in the case of many cosmetic formulations that are applied to the face or other exposed parts of the body, although it is also generally desirable that the cation (and anion) component not be visible even if applied to non-exposed portions of the body. It will be recognized that in some cases, particularly with colored facial skin care products such as blushes, blemish covers, lipsticks and the like, the formulation will be designed to be visible on the skin; in such cases, it is desirable that the cation component itself be "invisible," that is, that it not adversely change the appearance of the overall formulation as applied to the skin.

In this regard, clinical studies relating to the invention have shown that anti-irritant effects can be achieved using cation concentrations well below those concentrations that, as applied in a typical topical vehicle, result in a visible cation (or salt) residue on the skin. For example, a blended formulation of 500 mM strontium nitrate in a silicone-based vehicle (Dow Corning cyclomethicone [DC344]:cyclomethicone/dimethiconol [DC1401]cyclomethicone/dimethicone polyol [DC3225C]:water; 10:20:15:55) results in an opaque white lotion which typically leaves no visible residue when applied to the skin of a representative subject.

In another embodiment of the invention, the anti-irritant cation of the invention can be formulated in a form for topical oral administration to treat pain or irritation in the mouth, throat or other portions of the upper gastrointestinal system such as that due to sore throats, canker sores, gum irritation or inflammation or the like, including such irritation as may be exacerbated by spicy or acidic foods as, for example, in the case of ulcers or heartburn. Preliminary studies related to the invention have suggested that the oral formulations containing the strontium cation in a concentration comparable to those described for external topical application are effective in reducing sore throat pain. Furthermore, it is believed that the strontium cation (and its suitable oral salts) are generally tasteless at the concentrations described. Suitable forms for such oral administration include liquids (e.g. mouthwash, gargle or spray solutions), lozenges, tablets, pills and capsules. As with other topical forms described herein, the components used in such oral formulations (including the cation salts) should be chosen to be non-toxic. Methods for preparing oral formulations suitable for use in the present invention are well known in the art.

Clinical Results

The anti-irritant efficacy of the formulations of the present invention was tested and confirmed in numerous clinical trials, the results of which are described in the examples below. While these examples further illustrate various aspects and preferred embodiments of the invention as described herein, they are examples only, and should not be considered as limiting the scope of the invention as set forth in the claims.

EXAMPLE 1

Clinical Studies of Anti-Irritation Activity

The objective of the clinical trials was to determine whether and to what extent topical formulations of the strontium cation reduced or prevented skin irritation caused by certain severe skin irritants, including particularly lactic acid and glycolic acid (which are hydroxy acids), caproyl salicylic acid (a β-hydroxy acid ester) and capsaicin (an isolate from cayenne and paprika known for its skin-irritating properties). The trials were conducted in a double blind, randomized, vehicle-controlled manner. Various formulations of the invention were tested in over 740 people. The results confirm the highly reproducible anti-irritant activity of the formulations of the present invention.

a. Lactic Acid Irritation Trials

1. Protocol

The majority of the trials were conducted using lactic acid as the skin irritant, and proceeded generally as follows.

The subjects were women who had been screened and shown to exhibit normal to above normal susceptibility to irritation by the tested irritant. Tests were conducted in multiple panels of from 7 to 12 subjects each. Subjects were instructed not to wear any makeup or facial lotions to the clinic the day of testing. The subjects were instructed to wash their face with Ivory bar soap in the clinic prior to application of test solutions.

Lactic acid skin-irritant compositions were formulated in an appropriate vehicle prior to application to the skin of the subjects. In the majority of the tests, the irritant composition was 7.5% lactic acid dissolved in a 10% ethanol-in-water solution.

Test anti-irritant formulations containing measured amounts of strontium salts (concentration 250 mM) were applied either (a) 15 minutes prior to application to the skin of the skin-irritant ("pretreatment test") or (B) simultaneously with the application of the skin-irritant ("time zero test"). In the case of the time zero tests, the anti-irritant formulation included both the lactic acid irritant and the cation anti-irritant ingredient of the invention, whereas in the pretreatment tests the anti-irritant formulation was separately formulated (typically in Elizabeth Arden "Visible Difference Refining Toner," a commercially available alcohol-based cosmetic solution) and applied 15 minutes before application of the irritant composition. Controls were performed by applying corresponding formulation(s) (pretreatment and/or skin-irritant composition) with an equimolar amount of sodium chloride to a contralateral portion of the subject's skin. Typically, the test materials were applied to the face of the subject.

All test solutions (including controls) were applied in a double blind, randomized fashion using the prepared solutions as previously placed in coded vial designated for use on either the right or left side of the face (or other test area). Solutions were typically applied using a cotton swab (six strokes) or sponge applicator to the face and cheek area extending from the midline of the nose over to the center of the cheek and from the cheek bone down to the jaw line. Application was made first to the right side and then to the left.

Sensory assessment scores were recorded for each treated side of the subject's skin every minute for 15 minutes or until three consecutive scores of "zero" irritation were obtained. The following scaled scores were used for sensory assessment:

| Score | Description of Irritation |
|---|---|
| 0 | NO irritation |
| 1 | SLIGHT irritation<br>(Barely perceptible stinging, burning or itching) |
| 2 | MILD irritation --<br>(Definite stinging, burning or itching) |
| 3 | MODERATE irritation --<br>(Distinctly uncomfortable stinging, burning or itching; constantly aware of irritation) |
| 4 | SEVERE irritation --<br>(Continuous stinging, burning or itching, and intensely uncomfortable; would interfere with daily routine) |

Symptom scores were cumulated, separately for the cation-treated and control-treated areas, for each individual and also for the panel as a whole. Individuals not reporting a cumulative score of at least "7" on at least one treatment area were excluded (in a blinded fashion) from further analysis in order to ascertain anti-irritant efficacy with respect to the more severely-susceptible test subjects. From a practical standpoint, scores of "0" and "1" on the above scale would be considered highly desirable for a commercial product because such a response would likely not result in a consumer ceasing to use a product. Some consumers, in fact, might view the "barely perceptible" sensations represented by a score of 1 to be an indication that a facial treatment skin care product (especially an exfoliant) was working as advertised. By contrast, irritation scores of "2", "3" and "4" would likely often result in a consumer never purchasing the product again.

In those subjects and skin samples where an irritation was sensed, the irritation commonly involved a spectrum of burn-sting-itch reactions over time. For example, a subject might at first experience a sting, but moments later might experience an itch with no sting. Subjects experiencing higher levels of irritation (e.g. scores of "3" or "4") occasionally exhibited erythema (visually observable inflammation) in addition to sensory irritation effects.

2. Results

Clinical tests of over 740 subjects, performed as generally described above, demonstrated that the strontium cation has significant and reproducible anti-irritant effects, particularly if administered simultaneously with an irritant compound. The average inhibition of cumulative irritation for various cation salts of the invention (at 250 mM) are shown in the following tables.

| Cation Salt | Percent Inhibition |
|---|---|
| TIME ZERO TESTS | |
| Strontium chloride | 60% |
| Strontium nitrate | 65% |
| PRETREATMENT TESTS | |
| Strontium chloride | 25% |
| Strontium nitrate | 50% |
| Strontium acetate | 46% |

A representative set of test results from several subject panels, performed using cation concentrations of 250 mM, is set forth in the following tables.

Pretreatment Tests

| Cation | Anion | Salt Formula | Vehicle | Percent Inhibition |
|---|---|---|---|---|
| Strontium | Chloride | $SrCl_2$ | VIS DIFFERENCE | 20 |
| Strontium | Nitrate | $Sr(NO_3)_2$ | VIS DIFFERENCE | 56 |
| Strontium | Acetate | $Sr(CH_3CO_2)_2$ | VIS DIFFERENCE | 46 |

Time Zero Tests

| Cation | Anion | Salt Formula | Vehicle | Percent Inhibition |
|---|---|---|---|---|
| Strontium | Chloride | $SrCl_2$ | 10% EtOH | 58 |
| Strontium | Nitrate | $Sr(NO_3)_2$ | 10% EtOH | 64 |

Figure 2:
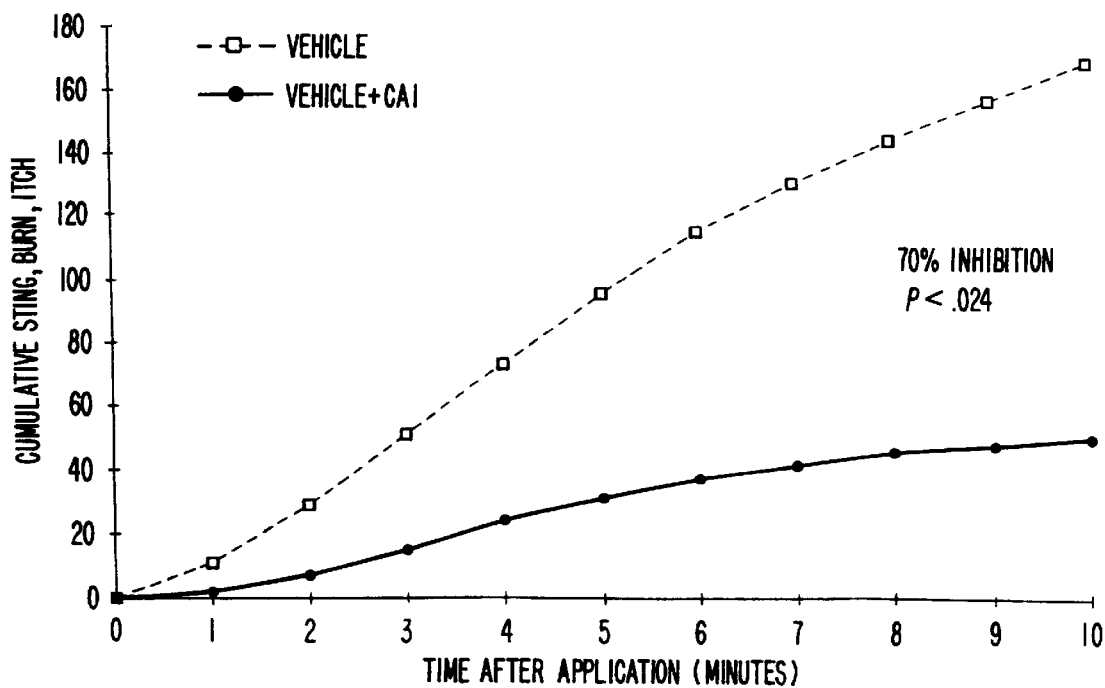
Figure 3:
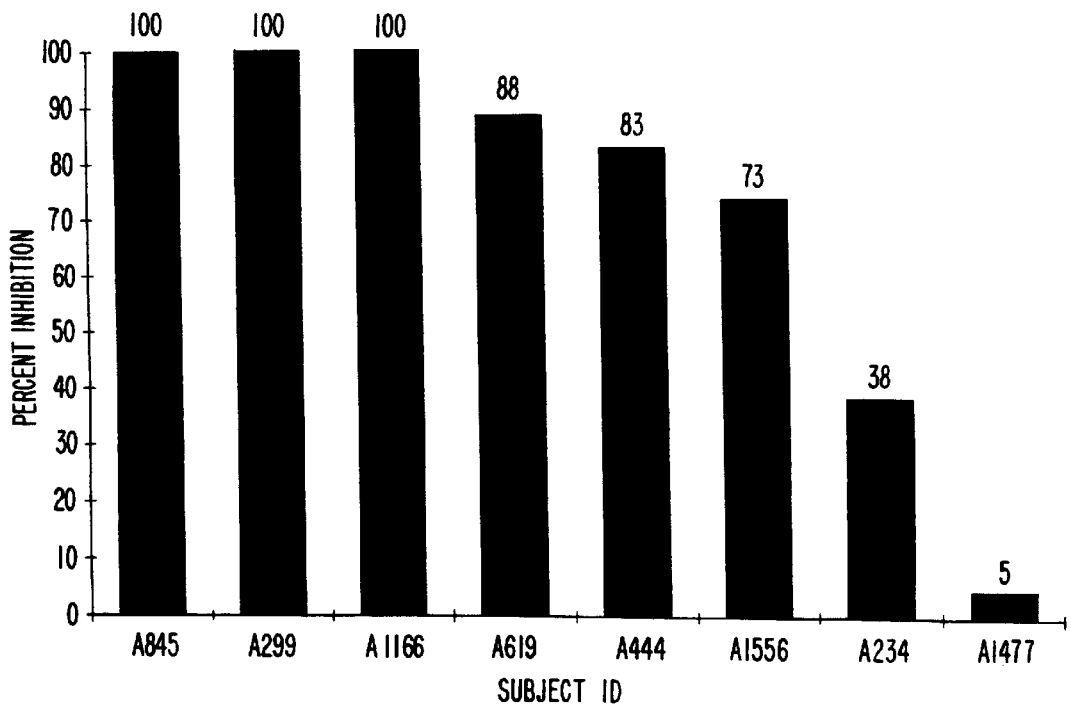
Figure 4:
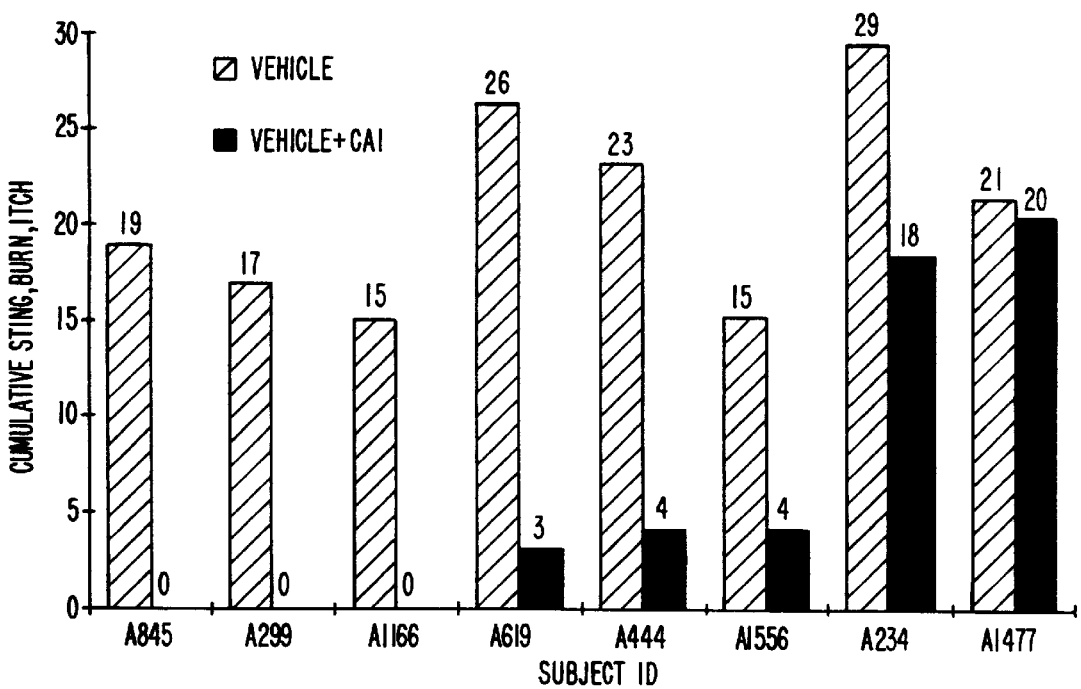

FIGS. 1 through 4 show more detailed experimental data for one panel test conducted using strontium nitrate (250 mM) as the anti-irritant salt component of the subject formulation (time zero test). FIG. 1 shows the time course of irritation responses for both cation-treated and non-treated (control) skin portions for the panel. FIG. 2 shows the cumulative irritation over time for the same panel, while FIGS. 3 and 4 show cumulative irritation suppression and treated/untreated irritation responses on a subject-by-subject basis. While individual responses vary somewhat, the overall efficacy of the subject formulation is clear.

b. Capsaicin Irritation Trials

Similar clinical trials were conducted to assess the efficacy of the cation of the invention to inhibit irritation induced by capsaicin. The clinical protocol was similar to that conducted with lactic acid, with the irritant/anti-irritant and control formulations being applied to the arms of the test subjects. The test compounds of the invention were formulated in Elizabeth Arden "Visible Difference Refining Toner", with the Toner mixed with equimolar sodium chloride serving as the control. The test solutions (and control) were provided in coded vials for application to either the right or left arms. A template (1.5 in.×4.0 in.) was placed on each forearm to mark the challenge area. The pre-treatment solutions containing the anti-irritant cation of the invention were applied to extend 1 inch beyond the marked challenge area in all directions and were allowed to dry for 5 minutes. 0.5 ml of 0.15% capsaicin cream or a swab moistened with capsaicin solution was thereafter applied to each arm by the clinical technician, who rubbed in the cream using gloved fingers. Application and scoring of test and control formulations was performed sequentially for each arm. Scoring was recorded every minute starting at 5 minutes post-application for 10 minutes and then every 5 minutes for 15 minutes (30 minutes total) for the cream, and every minute starting immediately for 15 minutes for the solution. Assessment was made using the irritation scale described above for the lactic acid test, and a simultaneous visual assessment of erythema was made by the monitoring technician.

Figure 5:
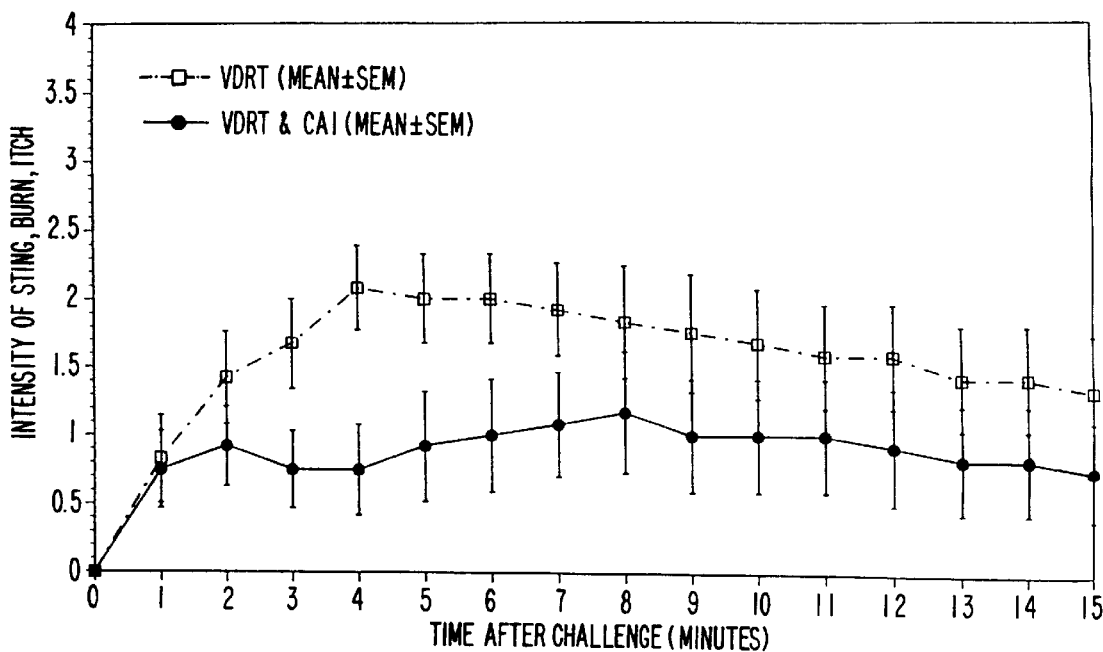
Figure 6:
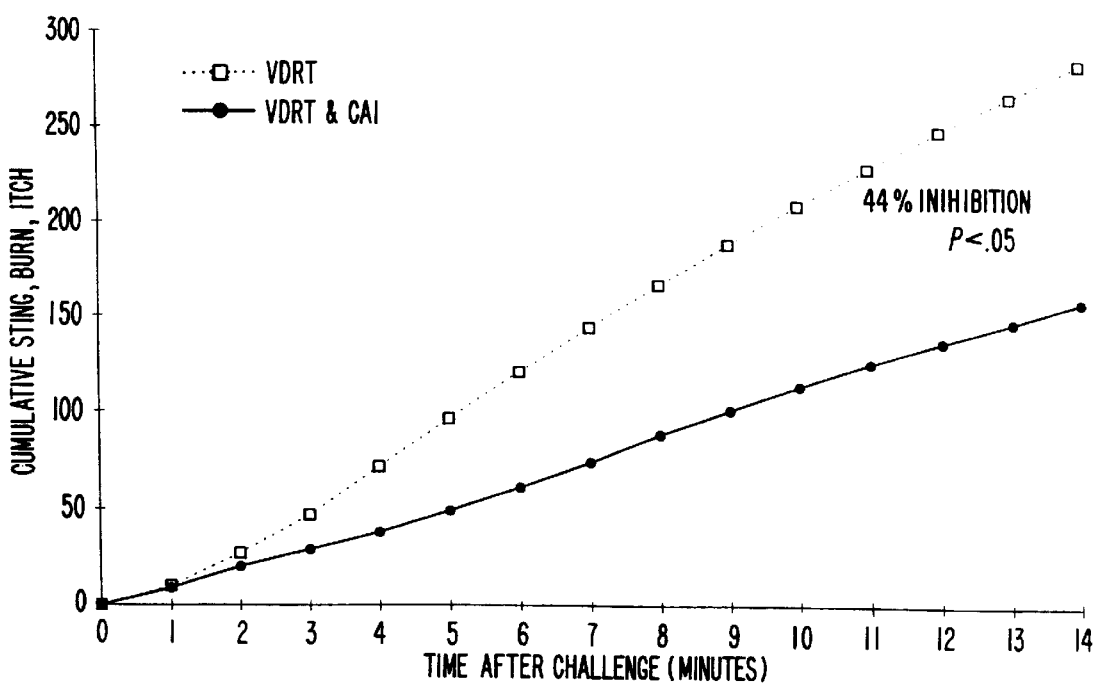
Figure 9:
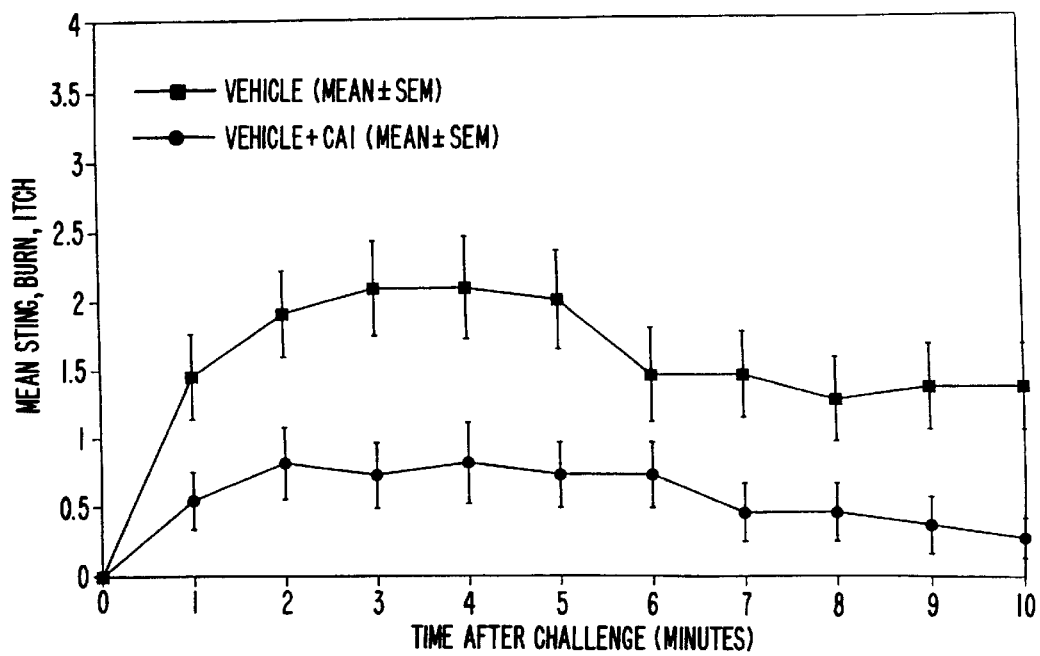
FIGS. 9 through 12 depict experimental data showing the time course of irritation responses (FIG. 9), the cumulative irritation over time (FIG. 10), and the subject-by-subject cumulative irritation suppression and irritation responses (FIGS. 11 and 12) for a panel of humans treated with 250 mM strontium nitrate (and control) in a glycolic acid skin irritation challenge.
Figure 10:
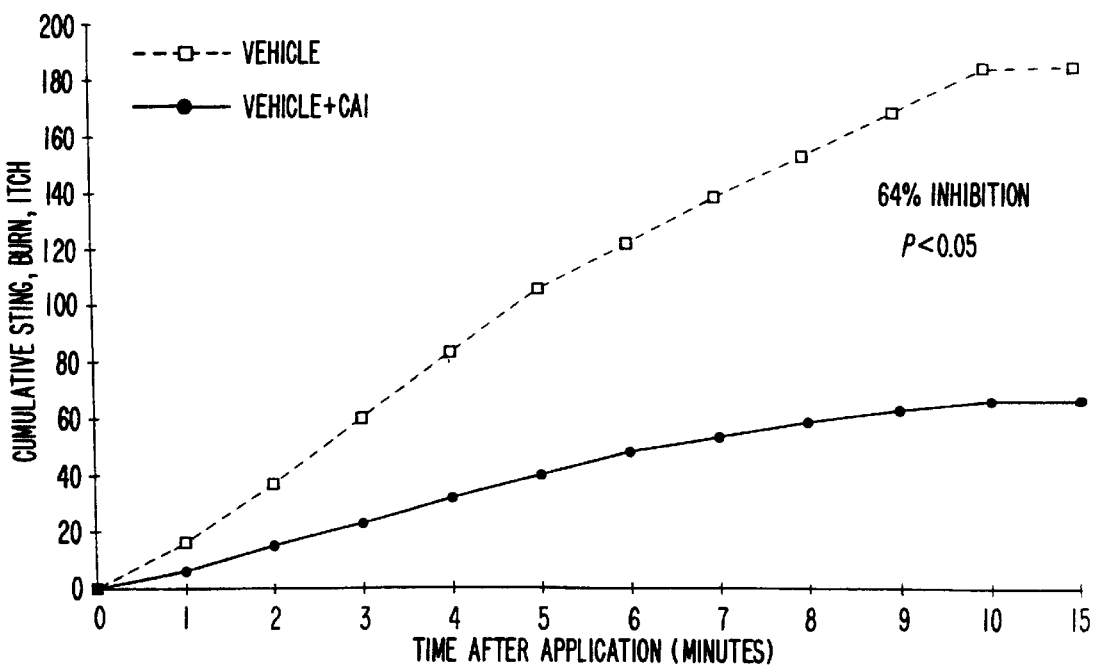
Figure 11:
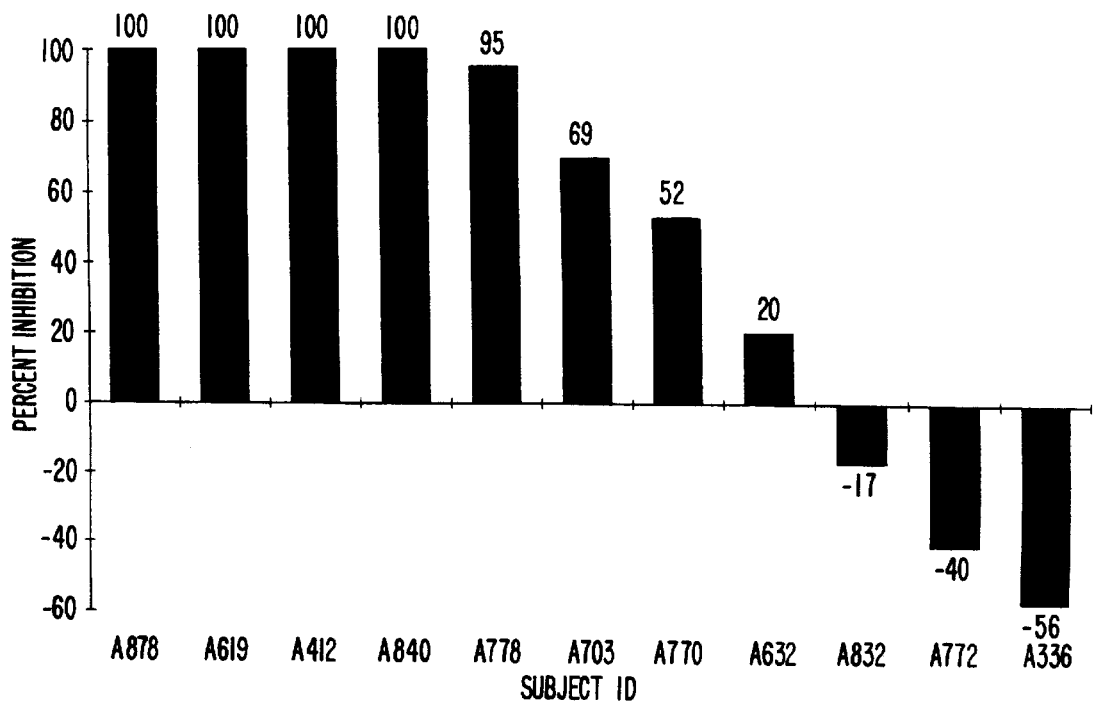
Figure 12:
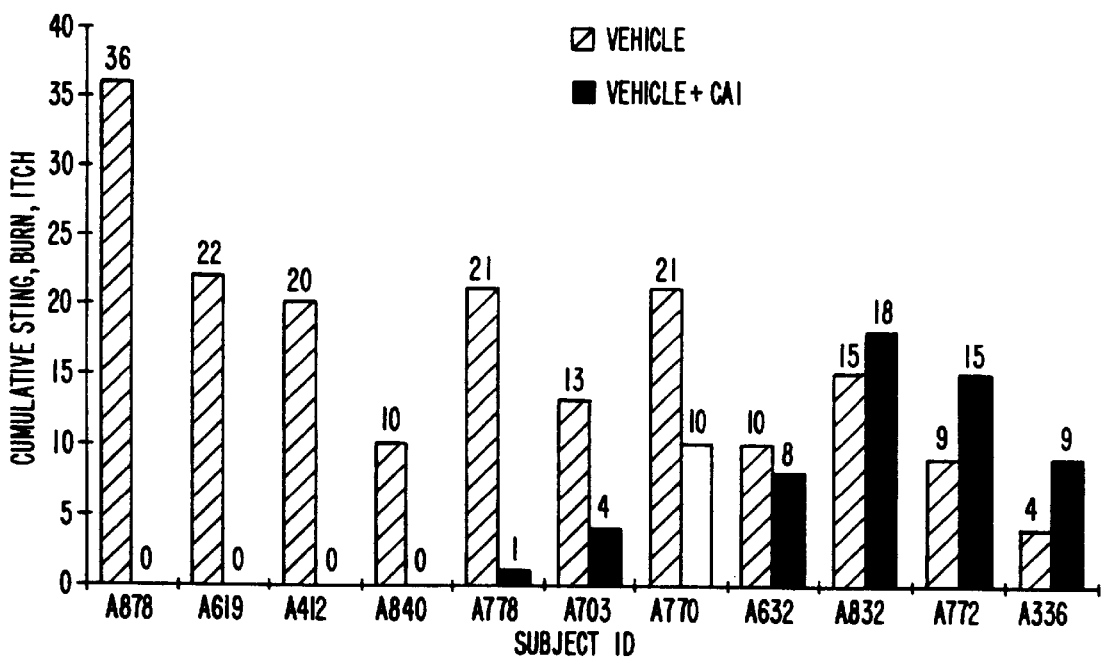

FIGS. 5 through 8 depict results from one representative panel tested in this trial, in which the anti-irritant cation component was applied in the form of strontium nitrate (250 mM). FIG. 5 shows the time course of irritation responses for both cation-treated and non-treated (control) skin portions for the panel. FIG. 6 shows the cumulative irritation over time for the same panel, while FIGS. 7 and 8 show cumulative irritation suppression and treated/untreated irritation responses on a subject-by-subject basis. Here again, while individual responses vary somewhat, the overall efficacy of the subject formulation is evident.

C. Glycolic Acid Irritation Trials

Following a protocol parallel to that of the lactic acid irritant trials described above, glycolic acid (6.0% in 10% ethanol-in-water) was applied as a skin irritant to subject panels. Strontium nitrate was co-administered as an anti-irritant (time zero testing), and was shown to inhibit cumulative irritation in subject panels by 64% to 84% at concentrations ranging from 250 mM to 500 mM. Time course and subject-by-subject data for one such test (cation concentration 250 mM) are presented in FIGS. 9 through 12.

d. Benzoyl Peroxide Irritation Trials

In this test, male and female subjects were recruited who had experienced a grade "2" or higher response in the sting/burn/itch lactic acid irritation protocol described above. Test subjects were limited to those who self-reported a sensitivity (sting, burn, itch) to benzoyl peroxide.

Subjects were instructed not to wear makeup or facial lotions on the day of testing. Those who had applied sunscreens to the face within 24 hours prior to testing, or who had taken any oral analgesic within 12 hours prior to testing, were disqualified. Subjects were instructed to wash their face with Ivory bar soap prior to application of test and control solutions. All materials were applied and scored in a double-blind, randomized fashion.

Facial irritation was induced by application of a 10% benzoyl peroxide wash product ("Oxy 10") to one side of the face. The other side of the face was treated with the same irritant composition containing 250 mM strontium nitrate as the test anti-irritant. Inactive ingredients in the benzoyl peroxide product included citric acid, cocamidopropyl betaine, diazolidinyl urea, methylparaben, propylparaben, sodium citrate, sodium cocoyl isethionate, sodium lauroyl sarcosinate, water, and xanthum gum.

The respective compositions were applied (from coded weighing vessels) using gloved fingers to the cheek area, first to the right side and immediately thereafter to the left. In order to maximize the irritation response above a baseline noise level, the solutions were left on the face for the entire 10 minutes of the study, rather than for only 1–2 minutes as instructed for the commercial benzoyl peroxide product.

To allow for adequate quantitation of the relatively low irritation levels in small numbers of subjects to be measured reliably and true differences in irritation to be determined, a differential scoring scale was developed. Using this method, each subject was asked to rate the magnitude of the difference in irritation response between the two sides of the face, as follows:

| Score | Relative Subjective Irritation |
| --- | --- |
| 0 | No irritation on either side of face, or No difference in irritation between the right and left sides of face. |
| 1 | Slight difference in irritation between fight and left sides of face; difference is barely noticeable and only evident after thinking about it. |
| 2 | Clear difference in irritation between right and left sides of face; difference is obvious and immediately evident. |

It was found that this simultaneous, differential scoring approach allowed for accurate comparisons to be made for the low levels of irritation associated with the present protocol, since it was much easier for the subjects to quantify the difference in irritation when both sides of the face were challenged simultaneously than to rate irritation sequentially on an "absolute" 0–4 scale as used in the lactic acid and glycolic acid protocols. On the other hand, when high levels of irritation are present, the use of sequential "absolute" scoring is preferred because it avoids uncertainty and "carry-over" effects from one side of the face to the other.

Figure 13:
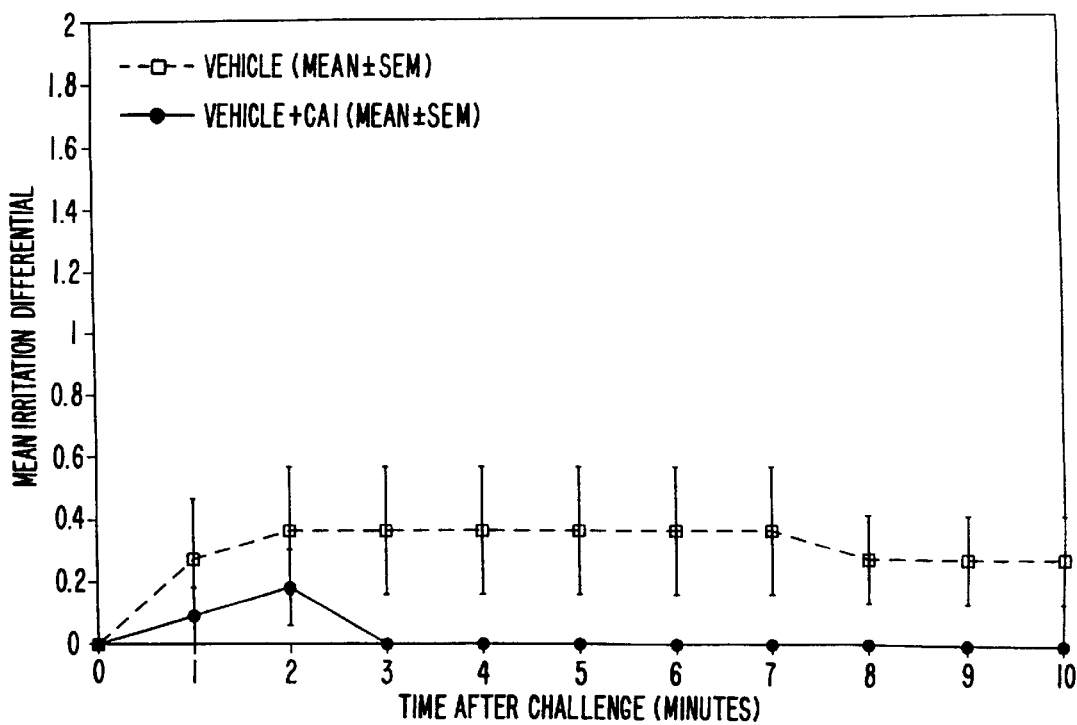
FIGS. 13 through 16 depict experimental data showing the time course of irritation differential responses (FIG. 13), the cumulative irritation differential over time (FIG. 14), and the subject-by-subject cumulative suppression of irritation differential and irritation differential responses (FIGS. 15 and 16) for a panel of humans treated with 250 mM strontium nitrate (and control) in a benzoyl peroxide skin irritation challenge.
Figure 14:
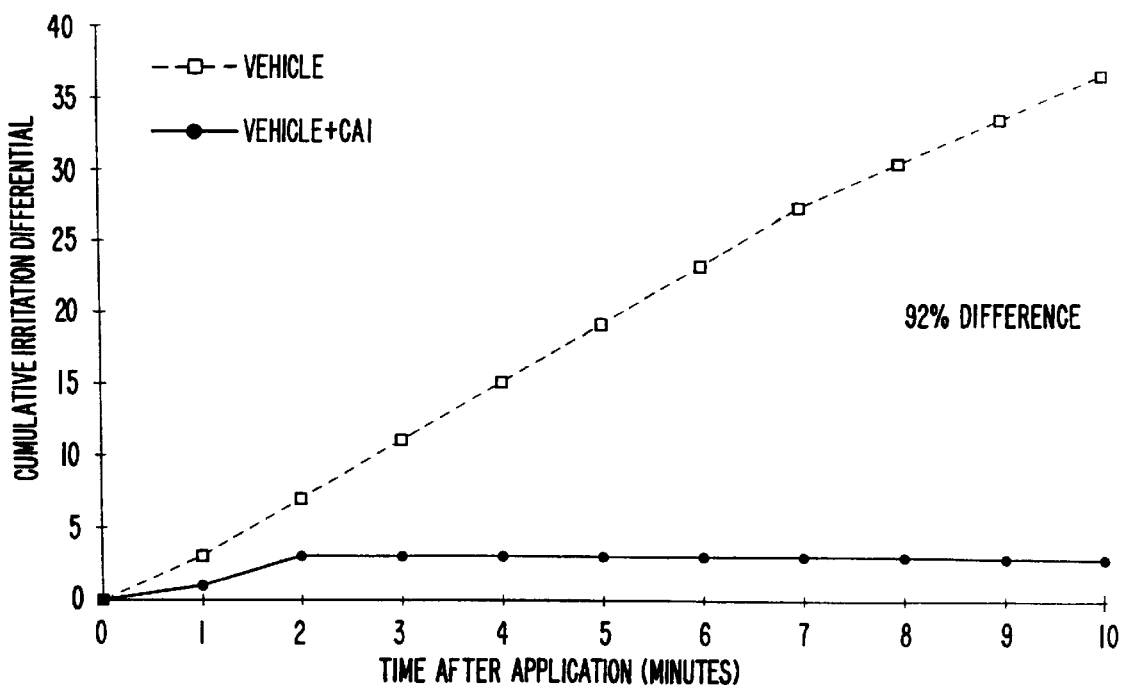
Figure 15:
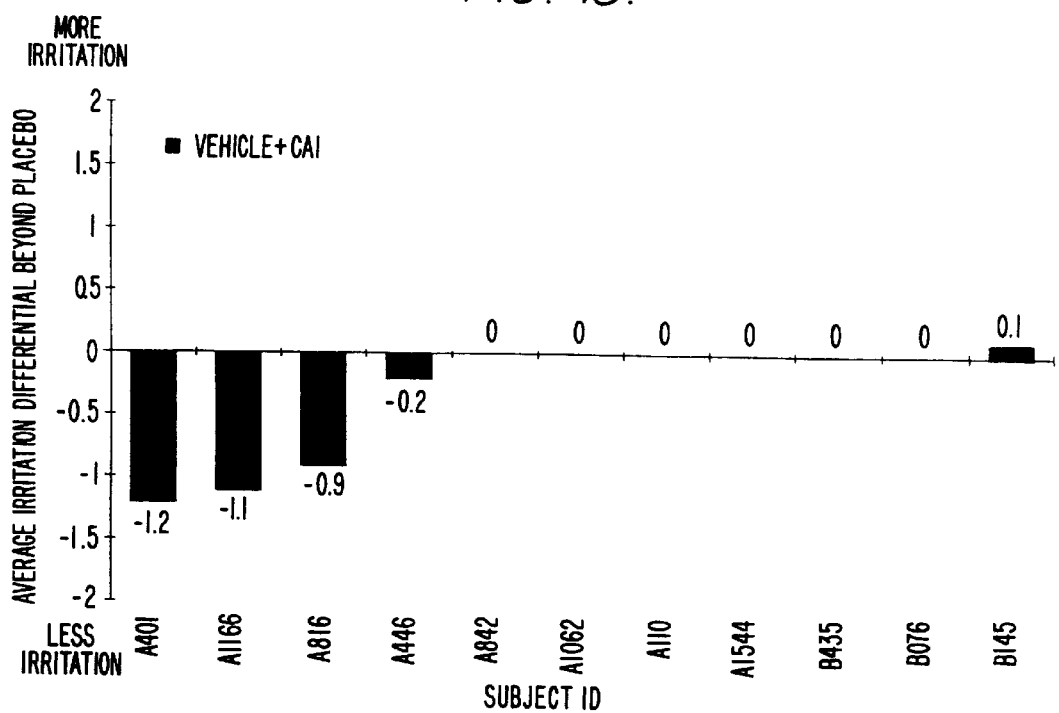
Figure 16:
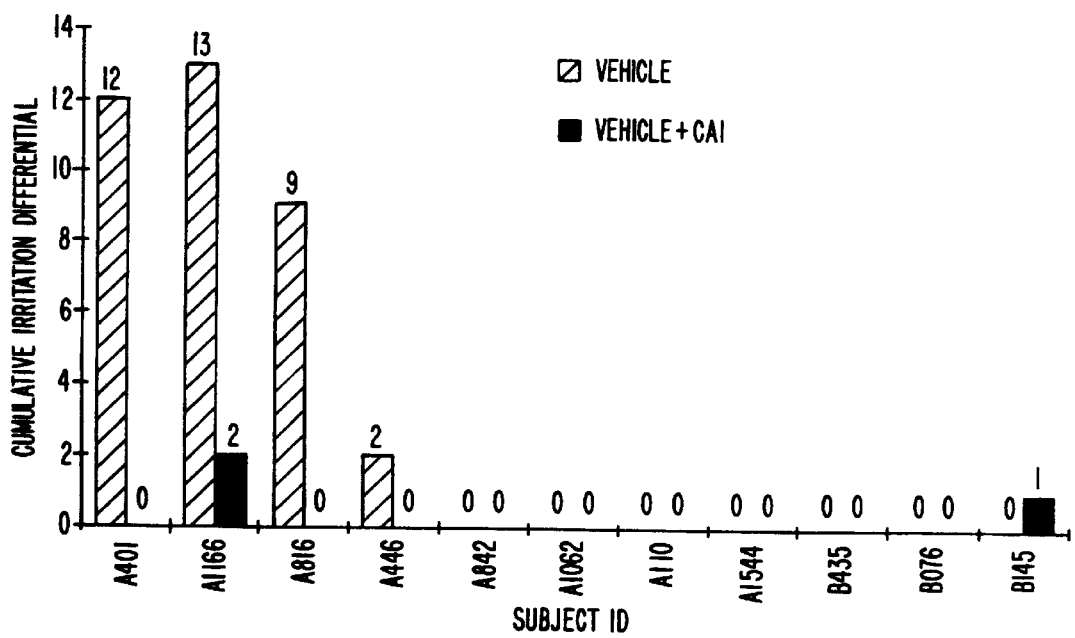

FIGS. 13 through 16 depict results obtained in this protocol using strontium nitrate as the anti-irritant cation component (250 mM). FIG. 13 shows the time course of differential irritation responses for both cation-treated and non-treated (control) skin portions for the panel. FIG. 14 shows the cumulative irritation over time for the same panel, while FIGS. 15 and 16 show cumulative irritation suppression and treated/untreated irritation responses on a subject-by-subject basis.

e. Post-Shaving Ocean Water Irritation

Ocean water is known to induce irritation in subjects with sensitive skin, particularly if the skin has been abraded by shaving or other means. The present test was performed to determine the ability of the present cation formulations to inhibit irritation of shaved skin due to ocean water.

Female subjects were instructed not to apply any sunscreen to their legs within 24 hours prior to testing, and not to ingest any oral analgesic medications within 12 hours prior to testing. The subjects were instructed to shave the lateral portions of their calves, spanning from the ankle to below the knee, with Ivory soap and a disposable razor prior to application of test, control and ocean water irritant solutions. All materials were applied and scored in a double-blind, randomized fashion.

Following shaving, 1 ml of pretreatment solution (test or control) was applied from coded vials to the respective right and left calves using cosmetic sponges. The test cation solution contained strontium nitrate (500 mM) in nanopure water (pH 4.5), and the control vehicle was nanopure water (pH 5.5). The solutions were allowed to dry for 2–3 minutes. Cosmetic sponges saturated with ocean water (La Jolla, Calif.) were used to apply ocean water challenge solutions to the right and left calves within the pretreated areas. The subjects were asked to rate levels of irritation (sting, burn or itch) on right and left calves, and irritation scores were recorded every minute for 10 minutes. The 0–4 scoring scale described above for the lactic acid irritation protocol was used in this test.

Figure 17:
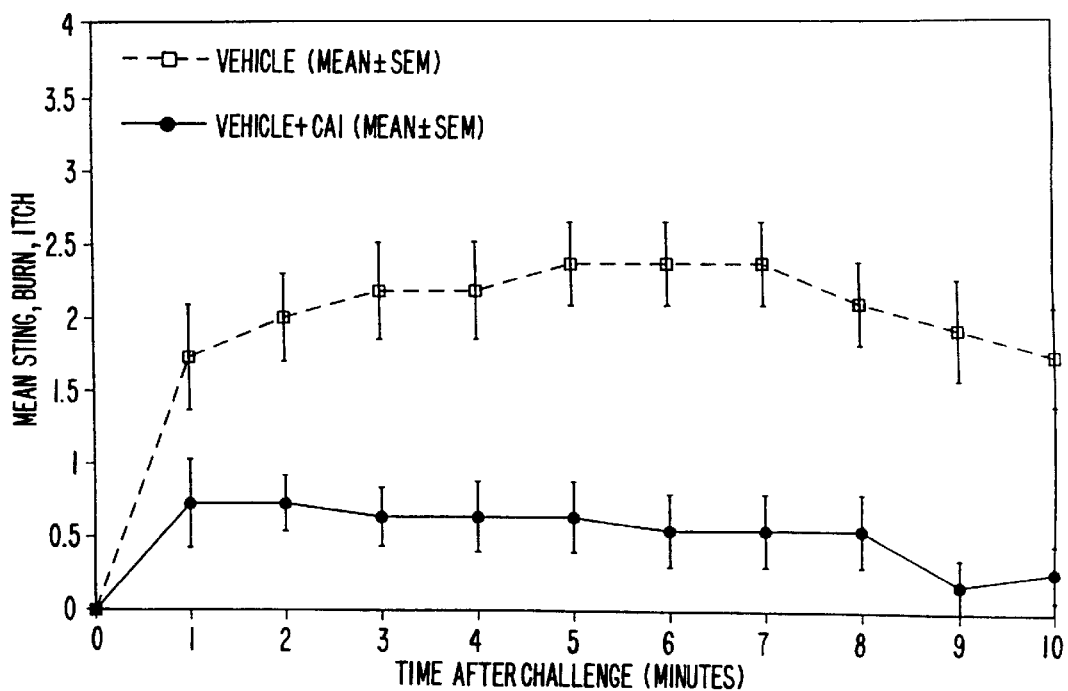
FIGS. 17 through 20 depict experimental data showing the time course of irritation responses (FIG. 17), the cumulative irritation over time (FIG. 18), and the subject-by-subject cumulative irritation suppression and irritation responses (FIGS. 19 and 20) for a panel of humans treated with 500 mM strontium nitrate (and control) in a post-shaving ocean water skin irritation challenge.
Figure 18:
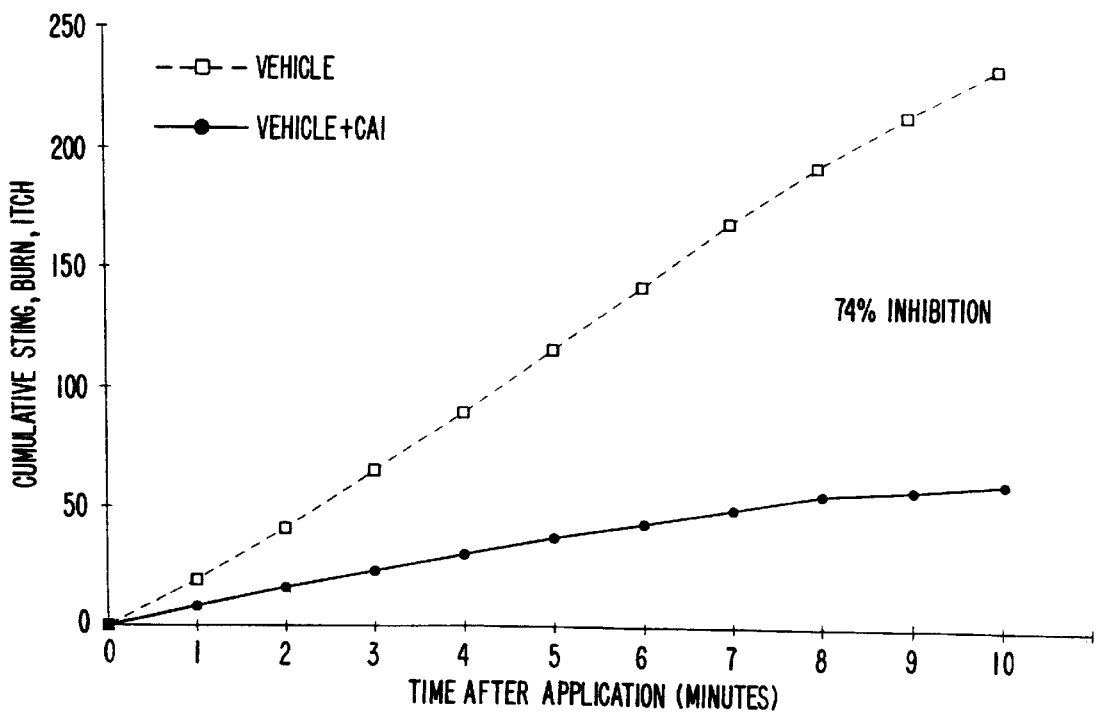
Figure 19:
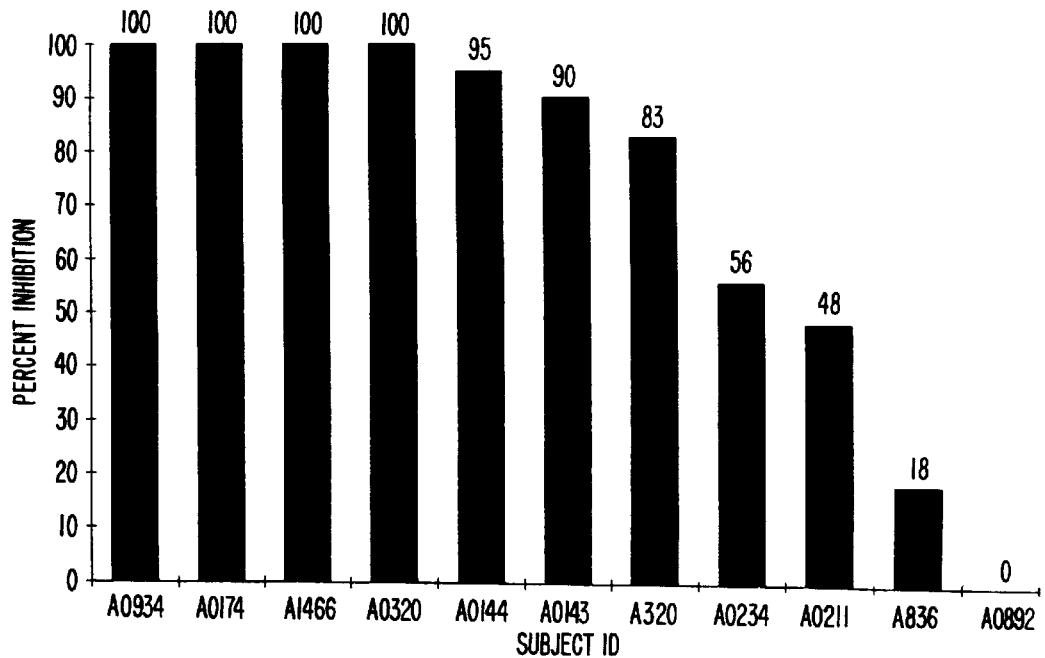
Figure 20:
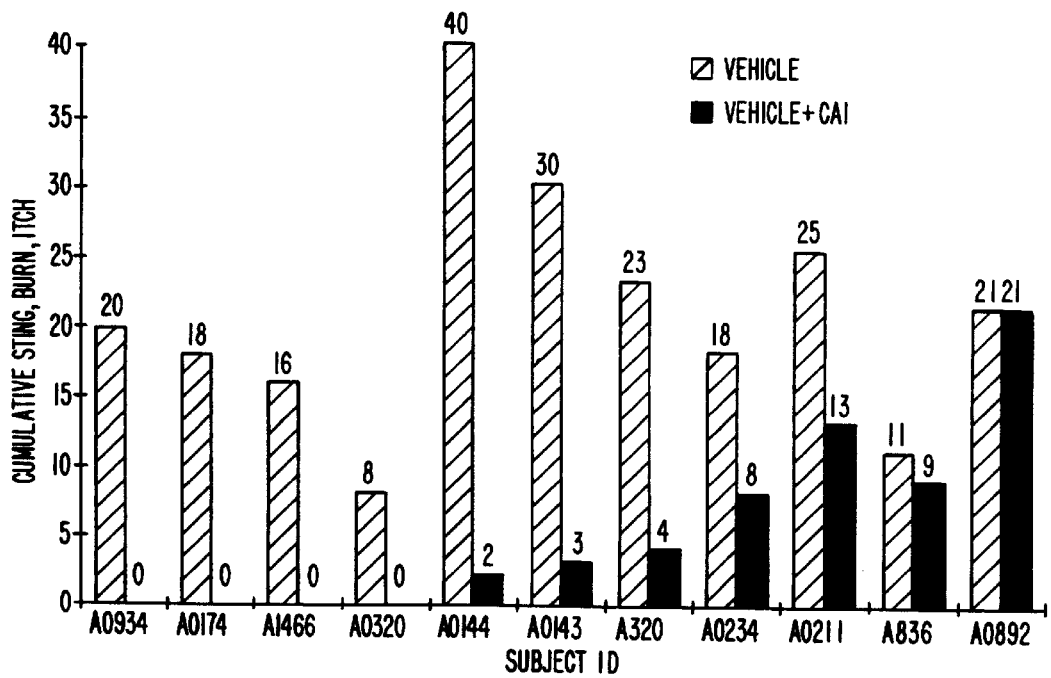

Irritation scores were cumulated for each individual and for the panel as a whole. FIG. 17 shows the time course of differential irritation responses for both cation-treated and non-treated (control) skin portions for the panel. FIG. 18 shows the cumulative irritation over time for the same panel, while FIGS. 19 and 20 show cumulative irritation suppression and treated/untreated irritation responses on a subject-by-subject basis.

f. Post-Shaving Lactic Acid Irritation

Following a protocol parallel to that of the post-shaving ocean water irritation test described above, a commercial lotion containing 5% lactic acid was applied to contralateral shaved calves of the subject females. The control solution was Vaseline Smooth Legs and Feet Lotion (containing water, lactic acid (5%), glycerin, isopropyl palmitate, PEG-40 stearate, cetyl alcohol, potassium hydroxide, steareth-2, magnesium aluminum silicate, lecithin, soya sterol, tocopheryl acetate, tetinyl palmitate, dimethicone, menthol, camphor, stearic acid, laureth-7, xanthan gum, polyacrylamide, C13–14 isoparaffin, corn oil, fragrance, DMDM hydantoin, iodopropynyl butylcarmamate, disodium EDTA, PG, and Ext. violet 2); the cation test formulation included strontium nitrate (500 mM) in the same Vaseline lactic acid lotion. 0.5 g of test and control solutions were applied with gloved fingers to the right and left calves. Subjects were asked to rate levels of irritation (sting, burn or itch) on the right calves, and irritation scores were recorded every minute for 10 minutes.

Figure 21:
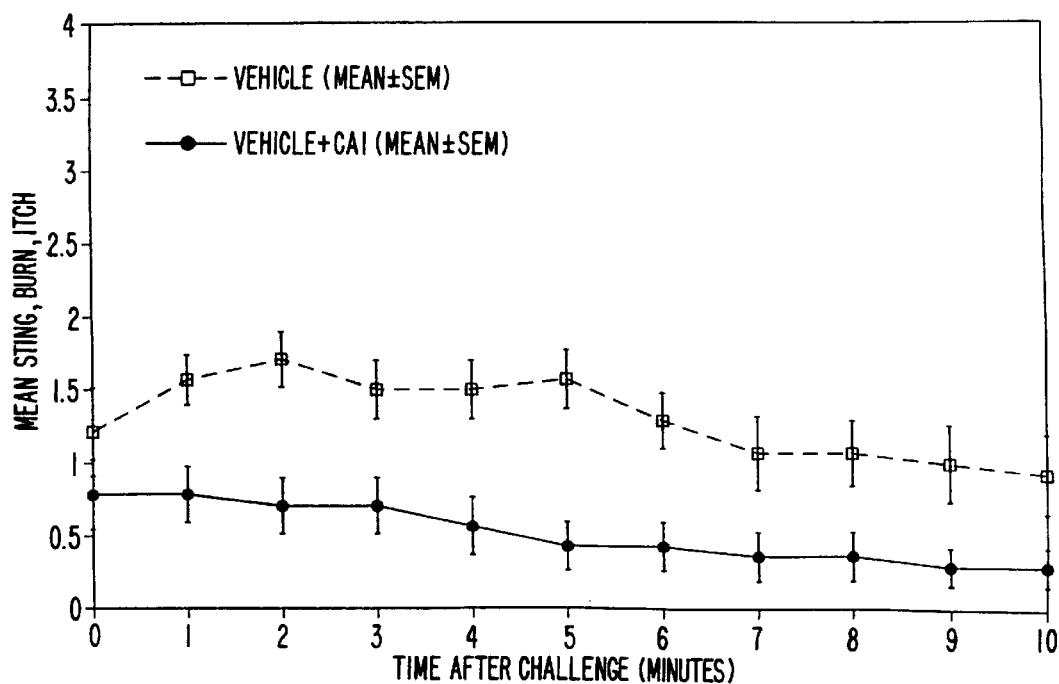
FIGS. 21 through 24 depict experimental data showing the time course of irritation responses (FIG. 21), the cumulative irritation over time (FIG. 22), and the subject-by-subject cumulative irritation suppression and irritation responses (FIGS. 23 and 24) for a panel of humans treated with 500 mM strontium nitrate (and control) in a post-shaving lactic acid skin irritation challenge.
Figure 22:
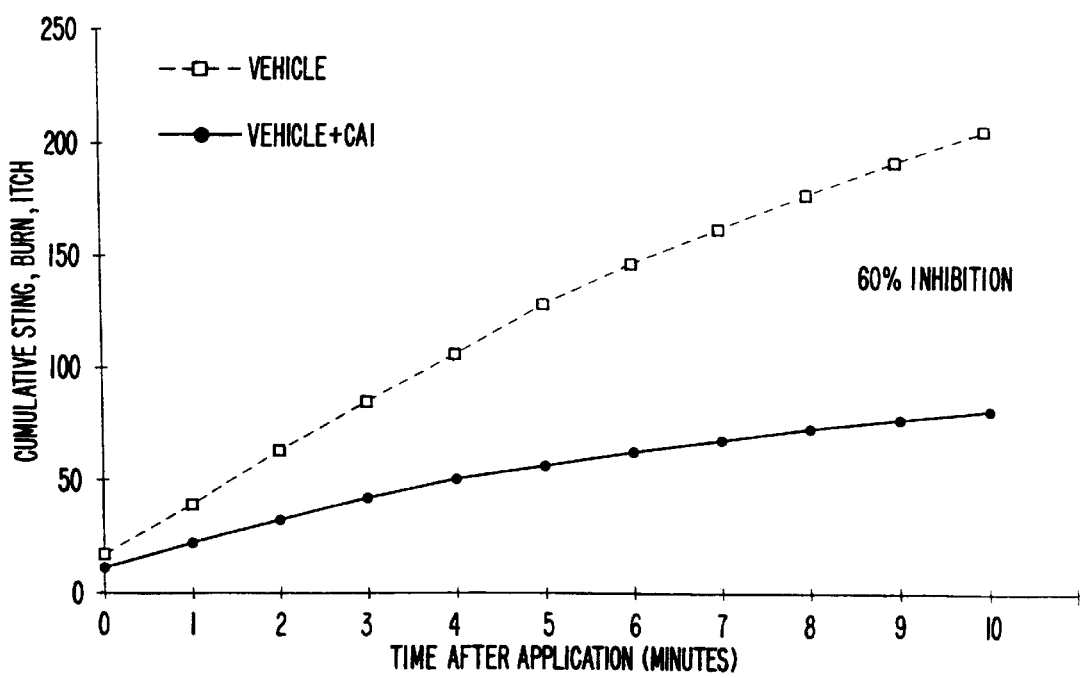
Figure 23:
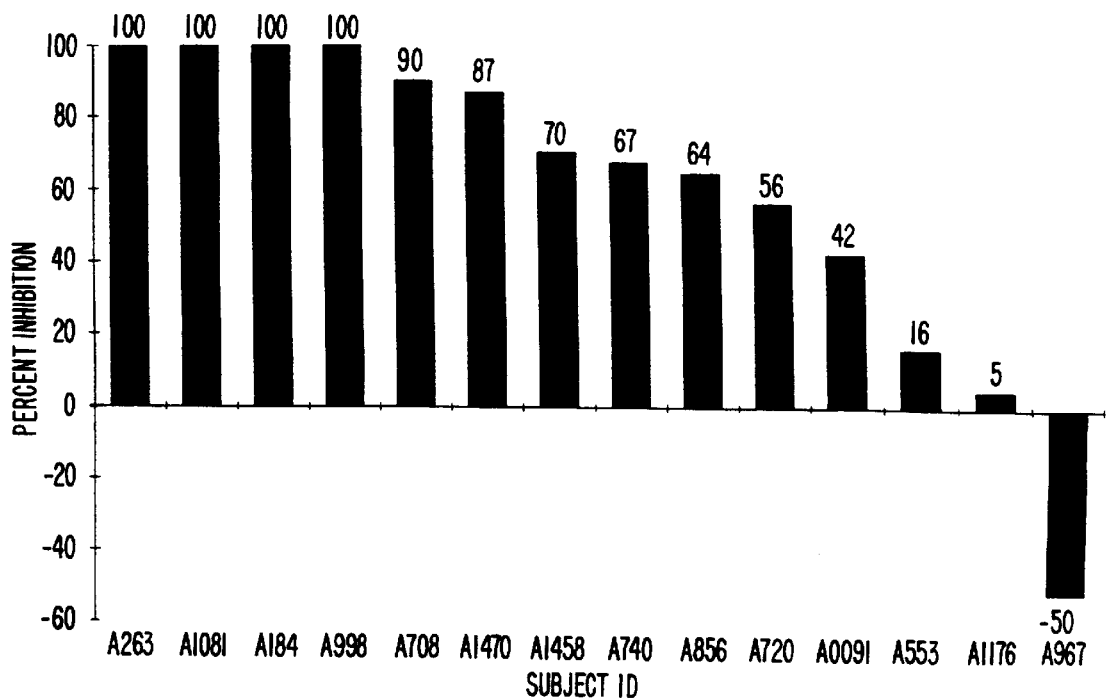
Figure 24:
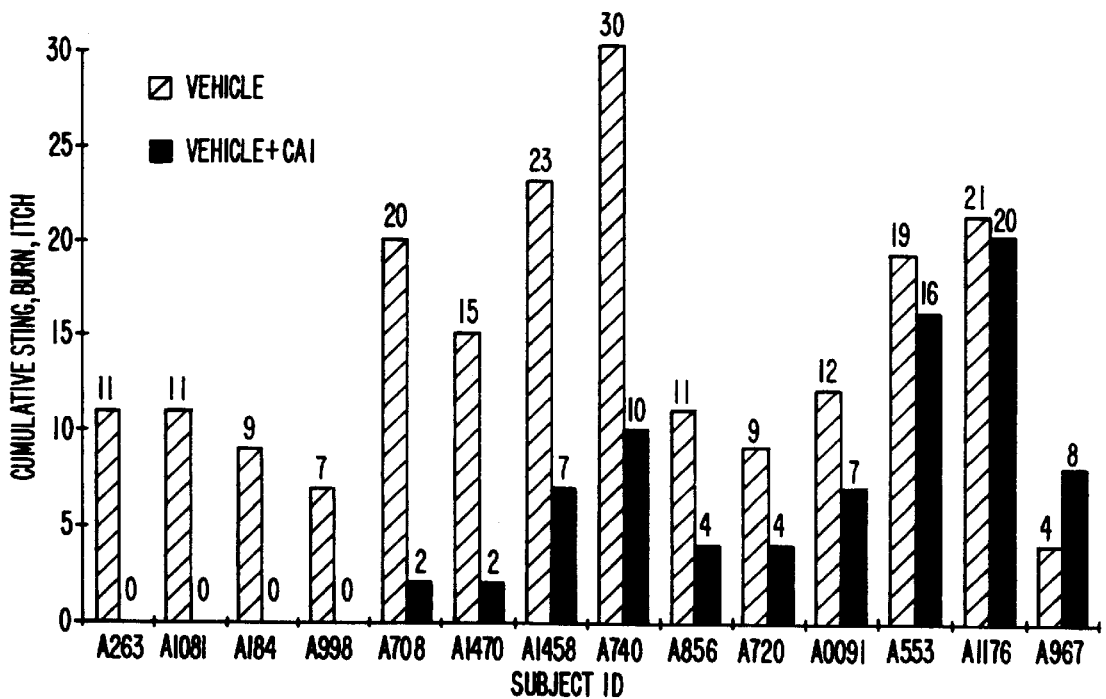

Irritation scores were cumulated for each individual and for the panel as a whole. FIG. 21 shows the time course of differential irritation responses for both cation-treated and non-treated (control) skin portions for the panel. FIG. 22 shows the cumulative irritation over time for the same panel, while FIGS. 23 and 24 show cumulative irritation suppression and treated/untreated irritation responses on a subject-by-subject basis.

EXAMPLE 2

Dose-Response Studies

Figure 25:
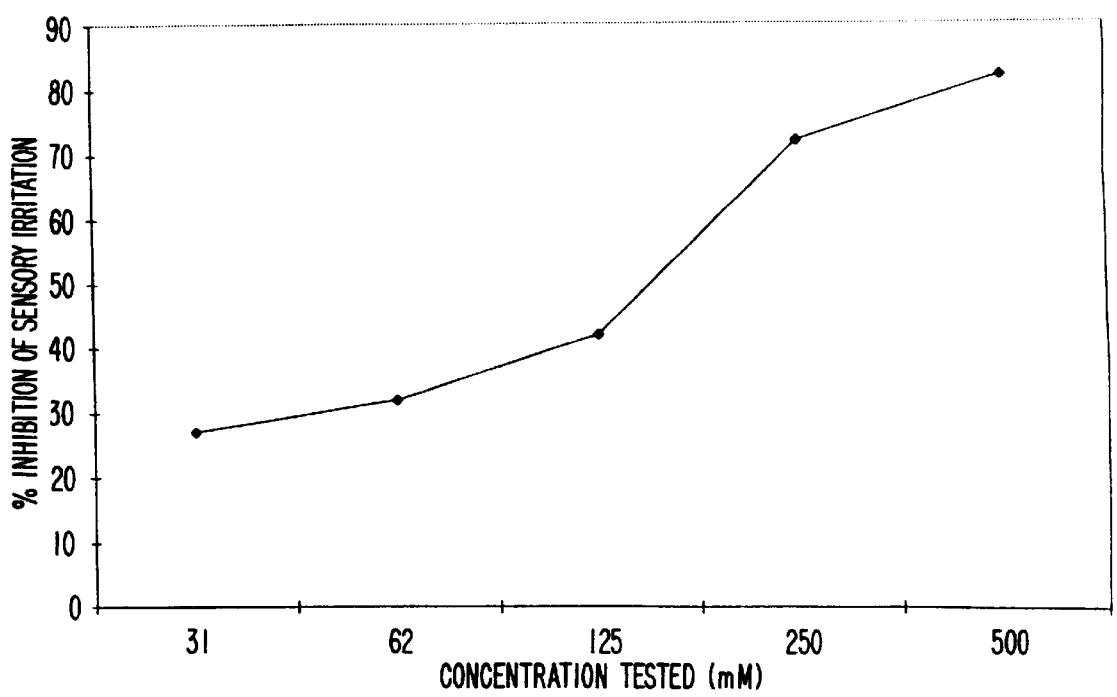
FIG. 25 depicts experimental data showing the cumulative irritation inhibition effects of strontium nitrate administered at varying concentrations (31–500 mM) in a lactic acid skin irritation challenge.

Additional studies of anti-irritant activity using varying concentrations of strontium cations were conducted in order to assess the dose-response behavior of the present formulations. The lactic acid irritation protocol described above was used, in which the anti-irritant cation component was strontium nitrate (31–500 mM). Cumulative irritation inhibition data are set forth in the following table, and are depicted graphically in FIG. 25.

| Concentration (mM) | Percent Inhibition |
| --- | --- |
| 31 | 27 |
| 62 | 32 |
| 125 | 42 |
| 250 | 72 |
| 500 | 82 |

EXAMPLE 3

Additional Formulation Examples

Cation salts of the invention were formulated at various concentrations in a number of commercially available topical vehicles, and also in various commercially available topical cosmetic products. The resulting mixtures generally did not alter the texture, color, consistency or other physical properties of the product, and could be used as formulations to inhibit topical irritation.

a. Silicone-Based Vehicles

A 500 mM strontium nitrate topical lotion was prepared as follows. 10.58 g of strontium nitrate was dissolved in 55 ml of deionized water. This solution was combined with 10 ml cyclomethicone (Dow Corning, "DC344"), 20 ml cyclomethicone/dimethiconol (Dow Corning, "DC 1401") and 15 ml cyclomethicone/dimethicone copolyol (Dow Corning, "DC3225C") and blended for 2–3 minutes. Imidizolidinyl urea (0.5%) was added as a preservative. An opaque white lotion (100 ml) resulted which, when applied to the skin of a fair (olive) skinned individual left no visible residue.

A 500 mM strontium nitrate topical gel was prepared as follows. 5.29 g of strontium nitrate was dissolved in 17 ml of deionized water. This solution was combined with 10 ml cyclomethicone (Dow Corning, "DC344"), 7.5 ml cyclomethicone/dimethiconol (Dow Corning, "DC 1401"), 7.5 ml cyclomethicone/dimethicone copolyol (Dow Corning, "DC3225C") and 8 ml PEG-8 and blended for 2–3 minutes. Imidizolidinyl urea (0.5%) was added as a preservative. A clear, thick gel resulted (50 ml).

A 1500 mM strontium nitrate topical gel was prepared as follows. 31.75 g of strontium nitrate was dissolved in 50 ml of deionized water. This solution was combined with 10 ml cyclomethicone (Dow Corning, "DC344"), 20 ml cyclomethicone/dimethiconol (Dow Corning, "DC1401") and 20 ml cyclomethicone/dimethicone copolyol (Dow Corning, "DC3225C") and blended for 2–3 minutes. Imidizolidinyl urea (0.5%) and benzyl alcohol (1%) were added as preservatives. A clear, thick gel resulted (100 ml) which, upon application to the skin of a fair-skinned subject, left a visible white residue.

A 1500 mM strontium nitrate topical gel with a glycerin component was prepared as follows. 31.75 g of strontium nitrate was dissolved in 60 ml of deionized water. This solution was combined with 5 ml cyclomethicone (Dow Corning, "DC344"), 10 ml cyclomethicone/dimethiconol (Dow Coming, "DC 1401 "), 15 ml cyclomethicone/dimethicone copolyol (Dow Corning, "DC3225C") and 10 ml glycerin and blended for 2–3 minutes. Imidizolidinyl urea (0.5%) was added as a preservative. A clear, thick gel resulted (100 ml).

b. Commercial Cosmetic Vehicles

Topical solution forms of strontium nitrate, strontium chloride and strontium acetate were prepared by combining various amounts of the named salts with Elizabeth Arden Visible Difference Refining Toner (an alcohol-containing solution). The concentrations achieved were shown to be effective to inhibit skin irritation as described in the protocols set forth above.

Similarly, other solution forms of strontium nitrate were prepared by combining anti-irritant effective amounts of the salt with Estee Lauder Clean Finish Purifying Toner Normal/Dry, Oil of Olay Refreshing Toner Cleanser and Toner, Mary Kay Refining Refreshener Formula 2, Clearasil Clearstick Max Strength, and Oxy-10 Benzoyl Peroxide Wash.

Topical lotion forms of strontium nitrate were prepared by combining anti-irritant effective amounts of the salt with Cheseborough-Ponds Lotions (CCB-3-83-L15), Vaseline Intensive Care Lotion Smooth Legs and Feet, and Lubriderm Moisture Recovery Lotion. Similarly, serum and cream forms of strontium nitrate were prepared by combining anti-irritant effective amounts of the salt with Mary Kay Revival Serum (with 15% lactic acid) and L'Oreal Vichy Novactia Cream (with 2% capryloyl salicylic acid), respectively.

The foregoing examples are not intended to limit the scope of the present invention, which is set forth in the following claims. In particular, various equivalents and substitutions will be recognized by those skilled in the art in view of the foregoing disclosure, and these are contemplated to be within the scope of the invention.

What is claimed is:

1. A composition for topical application to an animal subject comprising a topical vehicle;
   an irritant ingredient contained in an amount capable of inducing skin irritation in said subject; and
   an anti-irritant amount of at least about 50 mM of aqueous-soluble divalent strontium cation.

2. The composition of claim 1 comprising aqueous-soluble strontium cation in a concentration of from about 50 mM to about 2000 mM.

3. The composition of claim 1 comprising aqueous-soluble strontium cation in a concentration of from about 100 mM to about 1000 mM.

4. The composition of claim 1 comprising aqueous-soluble strontium cation in a concentration of from about 250 mM to about 500 mM.

5. The composition of claim 1 comprising an amount of aqueous-soluble strontium cation capable of inhibiting mean cumulative skin irritation attributable to said irritant ingredient in a susceptible human population by at least about 20%.

6. The composition of claim 5 wherein said inhibition of skin irritation represents an average reduction in one or more of sting, burn and itch in a susceptible human population upon topical application of said composition, as compared to the level of irritation induced in said population upon topical application of a control formulation containing said irritant ingredient in a vehicle without said strontium cation.

7. The composition of claim 1 comprising an amount of aqueous-soluble strontium cation capable of inhibiting by at least about 40% the cumulative skin irritation attributable to said irritant ingredient in at least 10% of the susceptible human population.

8. The composition of claim 7 wherein said inhibition of skin irritation represents an average reduction in one or more of sting, burn and itch in at least 10% of the susceptible human population upon topical application of said composition, as compared to the level of irritation induced in said at least 10% of the population upon topical application of a control formulation containing said irritant ingredient in a vehicle without said strontium cation.

9. The composition of claim 1 wherein said composition is a cosmetic product.

10. The composition of claim 9 wherein said composition comprises a skin exfoliant, skin peel or skin cell renewal agent.

11. The composition of claim 9 wherein said irritant ingredient comprises one or more members selected from the group consisting of carboxylic acids, keto acids, α-hydroxy acids, β-hydroxy acids, retinoids, peroxides, and organic alcohols.

12. The composition of claim 11 wherein said irritant ingredient comprises lactic acid or a salt thereof.

13. The composition of claim 11 wherein said irritant ingredient comprises glycolic acid or a salt thereof.

14. The composition of claim 11 wherein said irritant ingredient comprises salicylic acid or a salt thereof.

15. The composition of claim 11 wherein said irritant ingredient comprises a combination of lactic acid and salicylic acid, or salts thereof.

16. The composition of claim 11 wherein said irritant ingredient comprises capryloyl salicylic acid or a salt thereof.

17. The composition of claim 11 wherein said irritant ingredient comprises citric acid or a salt thereof.

18. The composition of claim 11 wherein said irritant ingredient is a retinoid selected from tretinoin, retinol, and retinal.

19. The composition of claim 11 wherein said irritant ingredient comprises benzoyl peroxide.

20. The composition of claim 11 wherein said irritant ingredient comprises acetic acid or a salt thereof.

21. The composition of claim 11 wherein said irritant ingredient comprises one or more of the group consisting of 1-pyrrolidone-5-carboxylic acid, capryloyl salicylic acid, α-hydroxy decanoic acid, α-hydroxy octanoic acid, gluconolactone, methoxypropyl gluconamide, oxalic acid, malic acid, tartaric acid, mandelic acid, benzylic acid, gluconic acid, pyruvic acid and phenol.

22. The composition of claim 11 wherein said irritant ingredient comprises trichloroacetic acid or a salt thereof.

23. The composition of claim 11 wherein the pH of the composition is in the range of 1 to 6.

24. The composition of claim 11 wherein the pH of the composition is in the range of 3 to 5.

25. The composition of claim 11 having a concentration of said irritant ingredient of from about 0.1% to about 50%.

26. The composition of claim 11 having a concentration of said irritant ingredient of from about 0.5% to about 20%.

27. The composition of claim 1 wherein said composition is an antiperspirant or deodorant product.

28. The composition of claim 1 wherein said composition is a sunscreen, tanning or sunburn treatment product.

29. The composition of claim 1 wherein said composition is an insect repellant product.

30. The composition of claim 9 wherein said composition is a shaving or hair removal product selected from the group consisting of depilatory, bracer, cream, foam, gel and aftershave products.

31. The composition of claim 9 wherein said composition is a hair care or hair treatment product.

32. The composition of claim 31 wherein said composition is selected from the group consisting of shampoo, conditioner, colorant, dye, bleach, permanent wave and hair straightener products.

33. The composition of claim 9 wherein said composition is selected from the group consisting of cleansers, astringents, toners, rinses, serums and masks.

34. The composition of claim 9 wherein said composition is a facial cosmetic product.

35. The composition of claim 9 wherein said composition is selected from the group consisting of creams, lotions and moisturizers.

36. The composition of claim 1 wherein said composition is selected from the group consisting of soaps and detergents.

37. The composition of claim 1 wherein said composition is a topical drug product.

38. The composition of claim 37 wherein said irritant ingredient is capsaicin.

39. The composition of claim 37 wherein said composition is selected from the group consisting of antibiotic, analgesic, contraceptive, anti-acne and anti-dandruff products.

40. The composition of claim 39 wherein said irritant ingredient is benzoyl peroxide.

41. The composition of claim 1 wherein said composition is formulated as a rectal or vaginal suppository, foam, cream, gel, ointment, enema or douche.

42. The composition of claim 1 wherein said composition is formulated for administration to the mouth, throat or lip.

43. The composition of claim 42 formulated as a lozenge, mouthwash or gargle.

44. The composition of claim 1 formulated as a liquid, gel, cream, emulsion, suspension or stick.

45. The composition of claim 1 formulated with a physical applicator.

46. The composition of claim 45 wherein said physical applicator is selected from the group consisting of cloths, tissues, swabs, bandages and wet wipes.

47. The composition of claim 1 wherein said composition is formulated for ocular administration.

48. The composition of claim 1 wherein said composition is formulated for administration to the respiratory system.

49. The composition of claim 1 wherein said composition is formulated for administration to the gastrointestinal system.

50. The composition of claim 1 wherein said composition is formulated for administration to the reproductive system.

51. The composition of claim 1 further comprising, as counteranions to said aqueous-soluble strontium cation, one or more topically acceptable anion species.

52. The composition of claim 51 further comprising, as counteranions to said aqueous-soluble strontium cation, one or more anion species selected from the group consisting of nitrate, halogen, carbonate, bicarbonate, hydroxide, oxide, peroxide, nitrite, sulfide, bisulfate, persulfate, glycerophosphate, hypophosphate, borate and titanate inorganic anions, and carboxylic acid, alkoxylate, amino acid, peptide, saturated and unsaturated organic acid, and saturated and unsaturated fatty acid organic anions.

53. The composition of claim 51 wherein said one or more of said counteranions is an organic anion selected from the group consisting of citrate, oxalate, acetate, gluconate, lactate, tartrate, maleate, benzoate, propionate, salicylate, ascorbate, formate, succinate, folinate, aspartate, phthalate, oleate, palmitate, stearate, lauryl sulfate, lanolate, myristate, behenate, caseinate, cyclamate, pantothenate, polyaminopolycarboxylates, saccharin, thioglycolate, laurate, methylparaben, propylparaben, ricinoleate and sorbate organic anions.

54. The composition of claim 51 wherein said anion species includes nitrate.

55. The composition of claim 51 wherein said anion species includes a halogen selected from chloride and fluoride anions.

56. The composition of claim 1 further comprising at least one second anti-irritant agent.

57. The composition of claim 56 wherein the total amount of said aqueous-soluble strontium cation and said second agent is capable of inhibiting mean cumulative skin irritation attributable to said irritant ingredient in a susceptible human population by at least about 20%.

58. The composition of claim 56 wherein the total amount of said aqueous-soluble strontium cation and said second agent is capable of inhibiting by at least about 40% the cumulative skin irritation attributable to said irritant ingredient in at least 10% of the susceptible human population.

59. The composition of claim 56 wherein said second agent is selected from the group consisting of potassium channel mediating, regulating or blocking agents, calcium channel blocking or regulatory agents, sodium channel blocking agents, steroids, non-steroidal anti-inflammatory agents, aloe vera, chamomile, α-bisabolol, Cola nitida extract, green tea extract, tea tree oil, licorice extract, allantoin, urea, caffeine and other xanthines, and glycyrrhizic acid.

60. An anti-irritant composition for inhibiting animal skin irritation comprising an anti-irritant amount of at least about 50 mM of aqueous-soluble divalent strontium cation and a topical vehicle, said anti-irritant composition being packaged with instructions directing the topical administration of the anti-irritant composition to an area of animal skin that is subject to skin irritation, and said anti-irritant composition further being effective, substantially simultaneously with said topical administration, to prevent or reduce skin irritation in said area of animal skin.

61. The composition of claim 60 comprising aqueous-soluble strontium cation in a concentration of from about 50 mM to about 2000 mM.

62. The composition of claim 60 comprising aqueous-soluble strontium cation in a concentration of from about 100 mM to about 1000 mM.

63. The composition of claim 60 comprising aqueous-soluble strontium cation in a concentration of from about 250 mM to about 500 mM.

64. The composition of claim 60 wherein said inhibition of skin irritation represents a reduction in skin irritation attributable to a pre-existing human skin disease or skin irritation condition.

65. The composition of claim 64 wherein said skin irritation is attributable to atopic dermatitis, non-atopic dermatitis, asthma, rhinitis, conjunctivitis, eczema, psoriasis or infectious disease.

66. The composition of claim 60 wherein said skin irritation is ocular irritation.

67. The composition of claim 60 wherein said skin irritation is respiratory system irritation.

68. The composition of claim 60 wherein said skin irritation is gastrointestinal system irritation.

69. The composition of claim 60 wherein said skin irritation is reproductive system irritation.

70. The composition of claim 60 wherein said skin irritation is irritation of a mucous membrane.

71. The composition of claim 60 wherein said skin irritation is irritation of epidermal skin.

72. The composition of claim 60 wherein said skin irritation is irritation of dermal skin.

73. The composition of claim 64 wherein said skin irritation is attributable to environmental exposure to one or more of sunlight, low humidity, wind, cold temperature, or hot and humid conditions.

74. The composition of claim 64 wherein said skin irritation is attributable to exposure to an irritating chemical agent.

75. The composition of claim 74 wherein said irritating chemical agent exposure is attributable to application of a topical product.

76. The composition of claim 75 wherein said product is selected from the group consisting of antiperspirant, deodorant, sunscreen, tanning, sunburn treatment, insect repellant, exfoliant, skin peel, skin cell renewal, fragrance, shaving or hair removal, hair care or hair treatment, cleanser, astringent, toner, rinse, serum, masks, facial cosmetic, cream, lotion, moisturizer, soap, detergent, and topical drug products.

77. The composition of claim 75 wherein said composition is packaged with instructions directing administration of said composition before, with or following administration of said topical product.

78. The composition of claim 74 wherein said irritating chemical agent exposure is attributable to insect sting or bite, or to plant exposure.

79. The composition of claim 64 wherein said skin irritation is attributable to one or more of shaving, skin cleansing or bathing, sweating, and physical skin trauma.

80. The composition of claim 60 wherein said skin irritation is attributable to dry skin.

81. The composition of claim 60 comprising an amount of aqueous-soluble strontium cation capable of inhibiting said skin irritation in subjects experiencing the same by an average of at least about 20%.

82. The composition of claim 60 comprising an amount of aqueous-soluble strontium cation capable of inhibiting said skin irritation by at least about 40% in at least 10% of the subjects experiencing the same.

83. The composition of claim 60 wherein said composition is formulated as a rectal or vaginal suppository, foam, cream, gel, ointment, enema or douche.

84. The composition of claim 60 wherein said composition is formulated for administration to the mouth, throat or lip.

85. The composition of claim 84 formulated as a lozenge, mouthwash or gargle.

86. The composition of claim 60 wherein said composition is formulated for ocular administration.

87. The composition of claim 60 wherein said composition is formulated for administration to the respiratory system.

88. The composition of claim 60 wherein said composition is formulated for administration to the gastrointestinal system.

89. The composition of claim 60 wherein said composition is formulated for administration reproductive system.

90. The composition of claim 60 formulated as a liquid, gel, cream, emulsion, suspension or stick.

91. The composition of claim 60 formulated with a physical applicator.

92. The composition of claim 60 further comprising, as counteranions to said aqueous-soluble strontium cation, one or more topically acceptable anion species.

93. The composition of claim 92 further comprising, as counteranions to said aqueous-soluble strontium cation, one or more anion species selected from the group consisting of nitrate, halogen, carbonate, bicarbonate, hydroxide, oxide, peroxide, nitrite, sulfide, bisulfate, persulfate, glycerophosphate, hypophosphate, borate and titanate inorganic anions, and carboxylic acid, alkoxylate, amino acid, peptide, saturated and unsaturated organic acid, and saturated and unsaturated fatty acid organic anions.

94. The composition of claim 92 wherein said one or more of said counteranions is an organic anion selected from the group consisting of citrate, oxalate, acetate, gluconate, lactate, tartrate, maleate, benzoate, propionate, salicylate, ascorbate, formate, succinate, folinate, aspartate, phthalate, oleate, palmitate, stearate, lauryl sulfate, lanolate, myristate, behenate, caseinate, cyclamate, pantothenate, polyaminopolycarboxylates, saccharin thioglycolate, laurate, methylparaben, propylparaben, ricinoleate and sorbate organic anions.

95. The composition of claim 60 further comprising at least one second anti-irritant agent.

96. The composition of claim 95 wherein said second agent is selected from the group consisting of potassium channel mediating, regulating or blocking agents, calcium channel blocking or regulatory agents, sodium channel blocking agents, steroids, non-steroidal anti-inflammatory agents, aloe vera chamomile, α-bisabolol, Cola nitida extract, green tea extract, tea tree oil, licorice extract, allantoin, urea, caffeine and other xanthines, and glycyrrhizic acid.

97. A method for inhibiting skin irritation associated with an irritant ingredient contained in an applied topical formulation, comprising topically administering to an animal subject the composition of claim 1.

98. A method for inhibiting skin irritation in an animal subject comprising topically administering to the subject the composition of claim 60.

99. The method of claim 98 wherein said composition is administered within about three hours prior to application to the subject of a second topical formulation containing an irritant ingredient.

100. The method of claim 98 wherein said composition is administered substantially simultaneously with application to the subject of a second topical formulation containing an irritant ingredient.

101. The method of claim 98 wherein said composition is administered to inhibit skin irritation attributable to a pre-existing animal skin disease or skin irritation condition.

102. The method of claim 98 wherein said skin irritation is ocular irritation.

103. The method of claim 98 wherein said skin irritation is respiratory system irritation.

104. The method of claim 98 wherein said skin irritation is gastrointestinal system irritation.

105. The method of claim 98 wherein said skin irritation is reproductive system irritation.

106. The method of claim 98 wherein said skin irritation is irritation of a mucous membrane.

107. The method of claim 98 wherein said skin irritation is irritation of epidermal skin.

108. The method of claim 98 wherein said skin irritation is irritation of dermal skin.

109. The method of claim 101 wherein said skin irritation is attributable to environmental exposure to one or more of sunlight, low humidity, wind, cold temperature, or hot and humid conditions.

110. The method of claim 101 wherein said skin irritation is attributable to exposure to an irritating chemical agent.

111. The method of claim 101 wherein said skin irritation is attributable to one or more of shaving, skin cleansing or bathing, and physical skin trauma.

112. The anti-irritant composition of claim 60 wherein said skin irritation is characterized by one or more of sting, burn or itch.

113. The anti-irritant composition of claim 60 wherein said skin irritation is itch.

* * * * *